(12) United States Patent
Reese

(10) Patent No.: US 8,342,400 B1
(45) Date of Patent: Jan. 1, 2013

(54) SYSTEMS CONTROLLED BY DATA BEARING RECORDS FOR MAINTAINING INVENTORY DATA

(75) Inventor: Rodney J. Reese, New Philadelphia, OH (US)

(73) Assignee: Diebold, Incorporated, North Canton, OH (US)

( * ) Notice: Subject to any disclaimer, the term of this patent is extended or adjusted under 35 U.S.C. 154(b) by 1147 days.

(21) Appl. No.: 12/283,436

(22) Filed: Sep. 11, 2008

Related U.S. Application Data

(60) Provisional application No. 60/993,571, filed on Sep. 13, 2007.

(51) Int. Cl.
| | |
|---|---|
| G06F 19/00 | (2006.01) |
| G06F 7/00 | (2006.01) |
| G06F 17/00 | (2006.01) |
| G06Q 30/00 | (2006.01) |
| G06Q 90/00 | (2006.01) |
| G08B 13/14 | (2006.01) |
| G08B 1/08 | (2006.01) |
| G08B 13/08 | (2006.01) |
| G08B 29/00 | (2006.01) |
| G05B 19/00 | (2006.01) |
| G05B 23/00 | (2006.01) |
| G08C 19/00 | (2006.01) |
| H04B 1/00 | (2006.01) |
| H04B 3/00 | (2006.01) |
| H04Q 1/00 | (2006.01) |
| H04Q 9/00 | (2006.01) |
| H04L 9/14 | (2006.01) |
| H04L 9/32 | (2006.01) |
| G06K 19/00 | (2006.01) |

(52) U.S. Cl. ............... 235/385; 235/381; 340/572.1; 340/545.6; 340/5.92; 340/5.8; 340/5.2; 340/539.12; 340/568.1; 700/236; 700/232; 700/237; 700/242; 700/244

(58) Field of Classification Search ............ 235/385, 235/375, 381; 340/572.1, 572.8, 572.9, 539.1–539.13, 340/568.1, 570, 5.92, 545.1, 545.6, 5.8–5.85, 340/5.2, 5.21, 5.3, 5.31; 705/2, 3, 26.9, 28; 700/231, 232, 236, 237, 240, 241, 242, 244
See application file for complete search history.

(56) References Cited

U.S. PATENT DOCUMENTS

| | | | |
|---|---|---|---|
| 4,967,928 A * | 11/1990 | Carter | 221/2 |
| 5,745,366 A * | 4/1998 | Higham et al. | 700/242 |
| 5,883,806 A * | 3/1999 | Meador et al. | 700/244 |

(Continued)

FOREIGN PATENT DOCUMENTS

JP 2007094864 A * 4/2007

(Continued)

*Primary Examiner* — Daniel Hess
*Assistant Examiner* — Suezu Ellis
(74) *Attorney, Agent, or Firm* — Ralph E. Jocke; Daniel D. Wasil; Walker & Jocke

(57) ABSTRACT

A registering and counting system operated in response to information included on data bearing records is used for maintaining inventory records related to narcotics items. Data corresponding to users is read through record reading devices (448, 452). Authorized users are allowed access to a narcotics vault (402). Narcotics holding containers (422) are removable from storage locations in drawers (416). Wireless transmitters on the containers operate in conjunction with wireless readers in the storage locations to enable a computer (458) to track the use of the narcotics items and operating parameters of the system.

24 Claims, 18 Drawing Sheets

U.S. PATENT DOCUMENTS

| | | | |
|---|---|---|---|
| 6,151,536 A * | 11/2000 | Arnold et al. | 700/237 |
| 6,294,999 B1 * | 9/2001 | Yarin et al. | 340/573.1 |
| 6,707,381 B1 * | 3/2004 | Maloney | 340/568.1 |
| 7,175,081 B2 * | 2/2007 | Andreasson et al. | 235/385 |
| 7,262,698 B1 * | 8/2007 | Frederick et al. | 340/545.6 |
| 7,518,516 B2 * | 4/2009 | Azevedo et al. | 340/572.1 |
| 7,693,603 B2 * | 4/2010 | Higham | 700/242 |
| 2004/0008123 A1 * | 1/2004 | Carrender et al. | 340/825.49 |
| 2006/0192001 A1 * | 8/2006 | Shaffer et al. | 235/385 |
| 2007/0272583 A1 * | 11/2007 | Kulkarni | 206/528 |
| 2008/0077274 A1 * | 3/2008 | Kim | 700/237 |
| 2008/0316045 A1 * | 12/2008 | Sriharto et al. | 340/825.49 |

FOREIGN PATENT DOCUMENTS

WO    WO 2007058048 A1 *   5/2007

\* cited by examiner

SYSTEMS CONTROLLED BY DATA BEARING RECORDS FOR MAINTAINING INVENTORY DATA

CROSS REFERENCE TO RELATED APPLICATION

This Application claims priority under 35 U.S.C. §119(e) of Provisional Application 60/993,571 filed Sep. 13, 2007 the disclosure of which is incorporated herein by reference.

TECHNICAL FIELD

This invention relates to registering and counting systems that are operated in response to information included on data bearing records and used for tracking inventory which may be classified in U.S. Class 235, Subclass 385. Specifically the exemplary embodiments relate to registering and counting devices used for maintaining inventory records for narcotics items.

BACKGROUND ART

Registering and counting devices that operate in response to data included on data bearing records are known. However, such devices may benefit from improvements.

OBJECTS OF EXEMPLARY EMBODIMENTS

It is an object of an exemplary embodiment to provide a system for maintaining inventory records.

If is a further object of exemplary embodiments to provide methods of operation of an inventory tracking system.

It is an object of an exemplary embodiment to provide a system and method for delivering outpatient pharmaceutical care in which a single pharmacist is responsible for providing care in multiple pharmacies.

It is a further object of an exemplary embodiment to provide a system and method for furnishing outpatient pharmaceutical care in which the pharmacist managing the care may do so from a location other than the pharmacy.

It is a further object of an exemplary embodiment to provide a system and method for furnishing outpatient pharmaceutical care in which a remote pharmacist directs one or more robots to prepare prescriptions or other controlled items locally, in secured locations. It is a further object of an exemplary embodiment to provide a system and method for furnishing outpatient pharmaceutical care in which the patient may access care through a stand-alone terminal within a store.

It is a further object of an exemplary embodiment to provide a system and method for furnishing outpatient pharmaceutical care in which the patient may access care through a drive-through terminal on the exterior of a store.

It is a further object of an exemplary embodiment to provide a system and method for furnishing outpatient pharmaceutical care with more accuracy than a traditional system by using automated mandatory verification before delivering the medication or other item to the patient.

It is a further object of an exemplary embodiment to provide a system and method for furnishing outpatient pharmaceutical care which provides increased assurance that each patient will be offered patient counseling with each item dispensed.

It is a further object of an exemplary embodiment to provide a system and method for furnishing outpatient pharmaceutical care which results in more effective counseling of patients by using a larger or multiple database of patient information.

It is a further object of an exemplary embodiment to provide a system and method for pharmaceutical outpatient care which results in more effective counseling of patients by using a systematically generated list of concerns that specifically relate to an individual patient and/or the item prescribed.

Further objects of exemplary embodiments will be made apparent in the following Detailed Description of Exemplary Embodiments and appended claims.

The foregoing objects are accomplished in an exemplary embodiment which permits a single pharmacist or other professional who can deliver prescription medications, who will be referred to herein as a "pharmacist," to simultaneously serve several individual pharmacies. In an exemplary embodiment a pharmacist will generally work at a location that is remote from most or all of the individual pharmacies being served. In order to accomplish this, the remote pharmacist will be in direct computer connection, over a network, with each of the individual pharmacies being served. Through this network, the pharmacist will be connected with user service stations, drug vaults, and a customer service computer located within each individual pharmacy. The connection will include CCTV connections to each of these locations within the individual pharmacies, permitting the pharmacist to observe a robot or other device preparing prescriptions in the drug retrieval vault and in the drug compounding vault, and to communicate directly with customers and local technicians.

In an exemplary embodiment, the pharmacist's computer is adapted to permit the pharmacist to control the robots in one or more drug vaults from a remote location. The remote pharmacist is in interactive communication with the robots in the individual pharmacies as the robots prepare the items that are to be dispensed to each customer.

In an exemplary embodiment of a pharmacy the remote pharmacist will have access to one or more processing and data storage devices containing individual patient histories for the group of pharmacies he or she serves, general information about the drugs which may be dispensed, the rules that apply to the various insurance plans accepted by each pharmacy, persons registered to prescribe medications, and the items stocked in each location. These data storage and processing devices may be in the same physical location as the remote pharmacist, or the pharmacist may be connected to these devices through one or more networks. The network used in an exemplary embodiment is separated from any external network by a pharmacist's computer which includes a firewall, or other means to prevent unauthorized access.

Each of the individual pharmacies served by a remote pharmacist is equipped with an automated drug preparation and compounding area, and may have one or more self-service customer terminals through which the patient can access pharmaceutical services. The individual pharmacies may also have a traditional customer service area, which is staffed by an individual. A computer in each local pharmacy controls and coordinates the network within that pharmacy. It includes a firewall or other means to prevent unauthorized access. Each of the individual pharmacies is connected to a remote pharmacist via a computer network system.

Customer terminals, if they are part of an embodiment of an individual pharmacy, may be walk-up terminals inside the store or drive-through terminals on the outside of the pharmacy. Customer terminals include a way for the patient to submit a prescription to be filled, to communicate with the pharmacist, to pay for the prescription, and to take delivery of the prescription. These functions may all be contained in a single customer terminal or split between two or more customer terminals. Some of the functions of a customer terminal will be performed using (1) dedicated input devices, such as a card reader, a prescription scanner, or a bar code reader; (2) dedicated output devices, such as printers adapted to print drug information sheets and receipts; and (3) interactive communication devices, such as Closed Circuit Television ("CCTV"), and intranet or internet connections. Most customer terminals will also include access to a pneumatic delivery system, which connects the parts of the local pharmacy so that objects can be sent between them.

An exemplary embodiment of the drug preparation area will generally include two vaults in which robots prepare the items requested. An exemplary embodiment of the first vault will include storage cells around the walls of the vault. These storage cells will contain the medications or medication components most commonly used in a particular pharmacy, and other items that must be dispensed through the pharmacy. Such an embodiment will also include a preparation area that includes various automated counting or measuring devices.

In the exemplary embodiment a relatively simple robot is located within the drug retrieval vault. The robot is adapted to perform one or more tasks necessary to prepare simple pharmaceutical orders. The robot is also adapted to perform one or more tasks necessary to deliver the raw ingredients for more complicated pharmaceutical orders to the drug compounding vault. Finally, the robot is adapted to package and deliver the prepared pharmaceutical order to the customer. Actions of the robot are directed by a pharmacist from a remote location.

In addition, an exemplary embodiment of a pharmacy using the exemplary system and method includes a drug compounding vault. This vault is used to prepare medications which cannot be delivered to the patient in the form in which they are stored in the pharmacy. The compounding performed may be minor, such as mixing water with a powder just before the medication is delivered to the patient. It may also be more complex, such as preparing an individualized medication from several ingredients.

An exemplary embodiment of a drug compounding vault includes the various devices that a pharmacist would need to compound drugs. The exemplary drug compounding vault is in direct connection with the drug preparation vault via a pneumatic delivery tube. An exemplary embodiment may also include a sophisticated medical robot, equipped with various sensor devices similar to those used in surgical robots.

An exemplary robot in an exemplary drug compounding vault is adapted to perform complex manipulations with raw ingredients, using traditional compounding tools, at the direction of a remote pharmacist. The robot is also adapted to retrieve ingredients sent to it by the robot in the drug retrieval vault and to return the compounded pharmaceutical item to the robot in the drug retrieval vault.

An exemplary embodiment of a pharmacy may also include a traditional customer service desk at which an individual may speak directly with a technician. In an exemplary embodiment of a system including this feature, the technician will gather the information from the patient, and transmit it to the remote pharmacist, using devices that may be similar to those available to the customer at a customer terminal. The look and feel of the interaction at a customer service desk will generally be similar to the look and feel of a traditional pharmacy interaction, with the exception that patients will receive counseling over the CCTV rather than face-to-face.

In addition, in an exemplary embodiment of a pharmacy using this method, a prescriber or a customer may use the telephone to request pharmaceutical care. Depending on the laws of the state, the technician at the service desk will either transmit the prescription in the form of an audio or digital recording to the remote pharmacist or will enter the information into the pharmacy computer which will then transmit it in facsimile form to the remote pharmacist. The system may also be configured to accept direct computer-to-computer transmissions of prescriptions from individual prescribers.

In other exemplary embodiments pharmacies may include user accessible narcotic holding vaults or other devices. Such narcotic holding devices include appropriate locking mechanisms to assure that access is limited to authorized persons and/or under authorized circumstances. In some exemplary embodiments narcotic items may be housed in containers that include wireless indicators thereon which provide signals that are useful for tracking such medical items. For example in some embodiments the taking and return of containers holding narcotic items can be tracked through operation of one or more computers. In still other exemplary embodiments sensors included in narcotics holding containers may operate to sense the weight or other properties of items housed therein. This may be useful in determining what has been removed from various containers. In still other exemplary embodiments containers may include programmable devices and memories which are operative to record information concerning activities related to containers within the programmable memory. This may further facilitate tracking activities. Further in some exemplary embodiments the systems may facilitate the monitoring of the taking of narcotic items for use in filling prescriptions for patients, either by a remote pharmacist or other individuals or tracking systems.

Various approaches may be used in various embodiments.

DETAILED DESCRIPTION OF EXEMPLARY EMBODIMENTS

Figure 1:
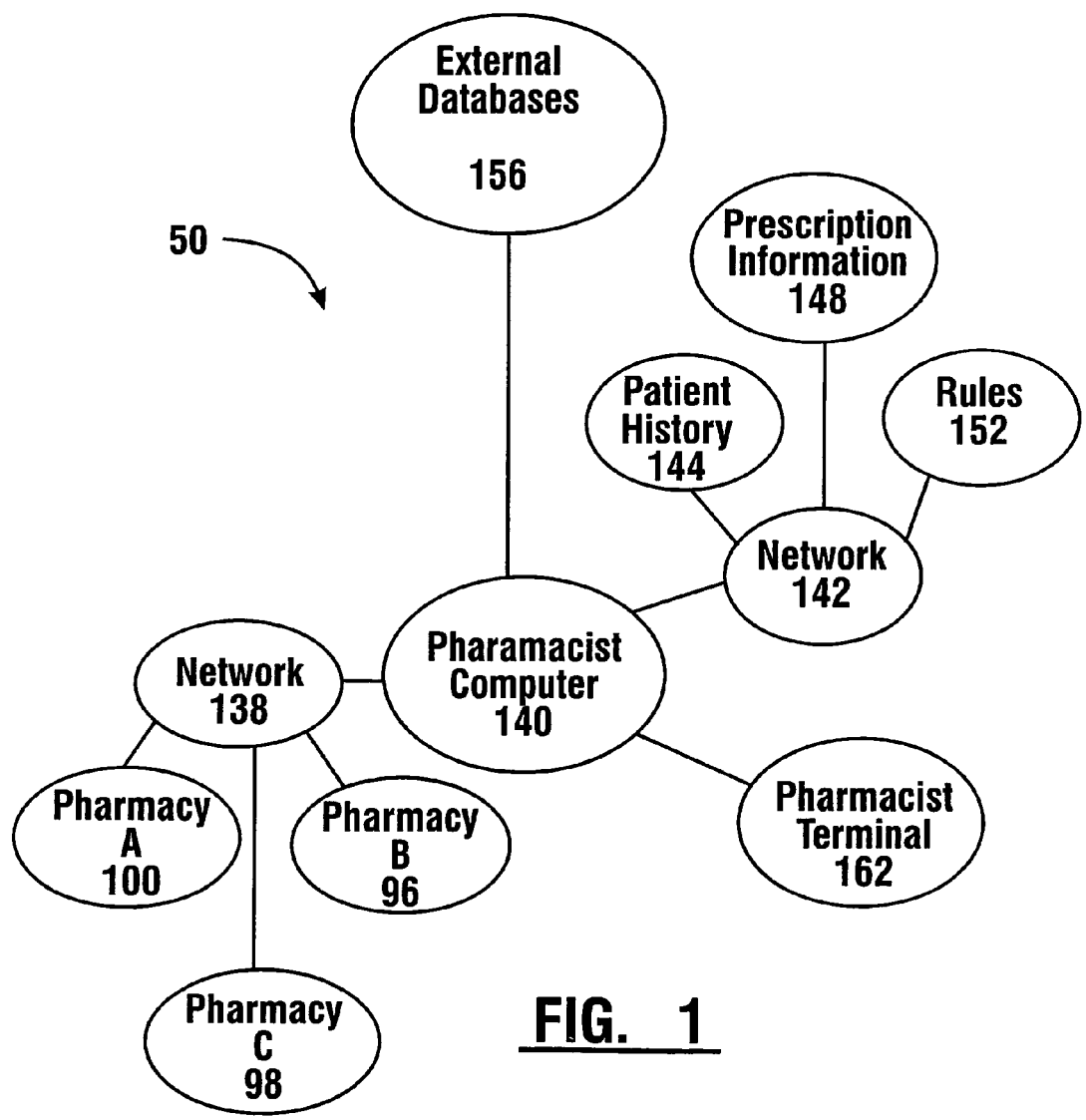
FIG. 1 is a schematic representation an exemplary pharmaceutical system.

Referring now to the drawings and particularly to FIG. 1, there is shown therein a schematic representation of an exemplary embodiment of a pharmaceutical system, generally designated by reference numeral 50. The pharmaceutical system 50 comprises a remote pharmacist computer 140, operatively linked over a network 138 to several individual pharmacies 96-100. In addition, the remote pharmacist computer may also be linked directly, or through one or more networks, to various databases which are represented schematically as external databases 156, patient history 144, prescription information 148, and rules 152.

Figure 2:
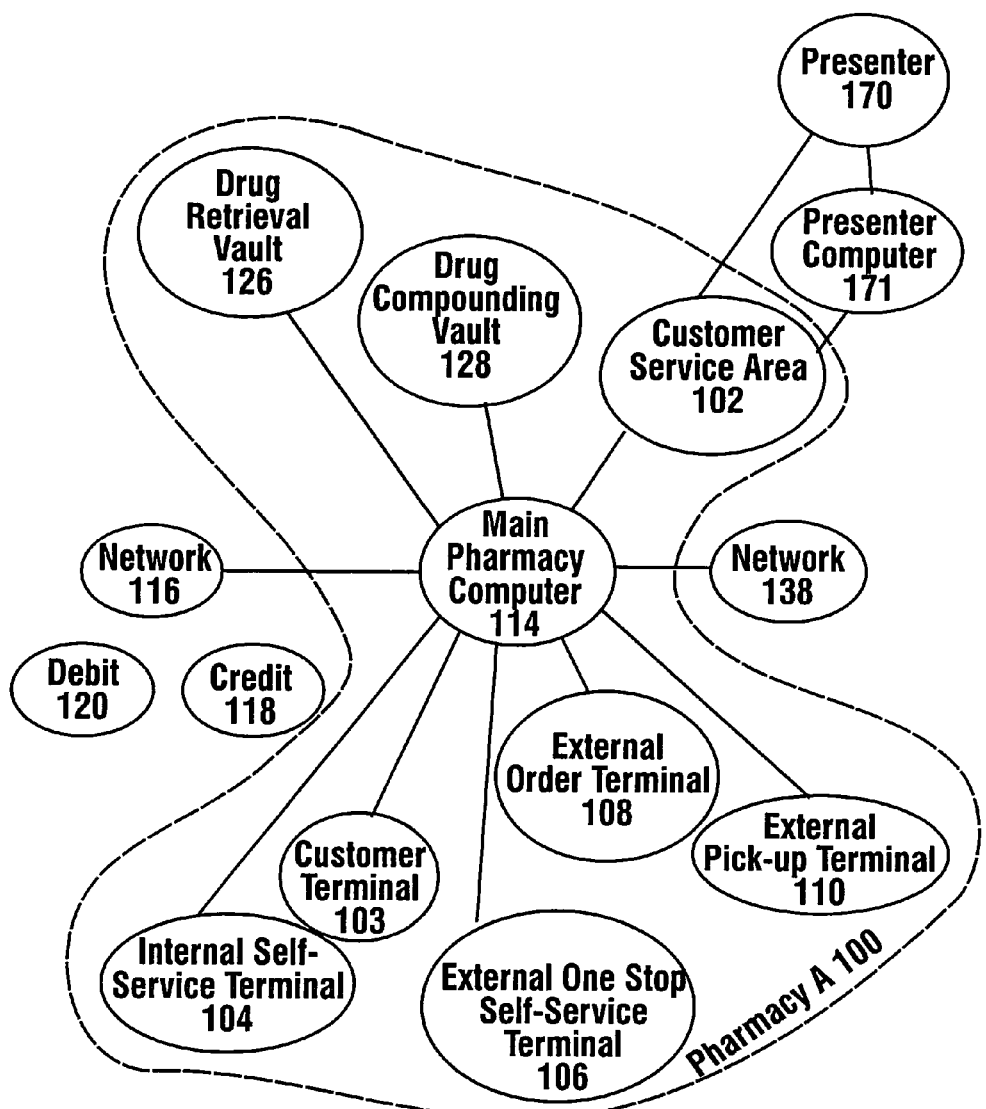
FIG. 2 is a schematic representation of an exemplary pharmacy.
Figure 3:
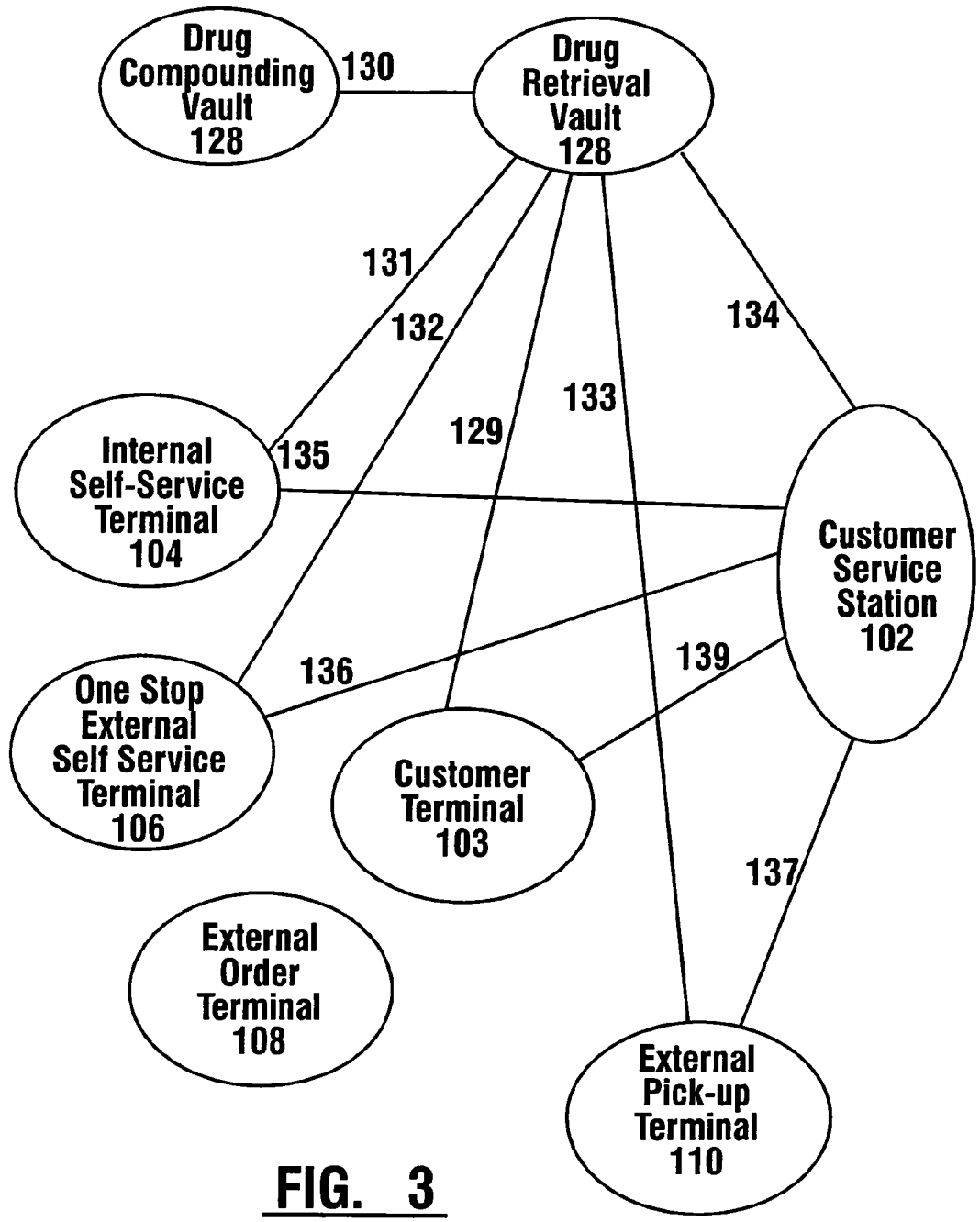
FIG. 3 is a schematic representation of the pneumatic delivery system connections.

A portion of the exemplary pharmaceutical system, an individual pharmacy, is illustrated in more detail in FIG. 2. The pharmacy is generally designated by reference numeral 100. Pharmacy 100 includes a customer service area 102, a drug retrieval vault 126, a drug compounding vault 128, and one or more customer terminals, such as an internal self-service terminal 104, a one-stop external self-service terminal 106, an external order terminal 108 or an external pickup terminal 110. A generic customer terminal 103 is illustrated in FIGS. 2 and 3, and should be understood to be interchangeable with any of the specialized terminals 104-110. Any reference herein to a customer terminal 103 should be understood to be a reference to any of the terminals 104-110. Any reference herein to customer terminals 103 should be understood to be a reference to any appropriate combination of terminals 104-110.

The exemplary pharmacy 100 also includes at least one pharmacy computer 114 electronically connected to and coordinating one or more customer terminals 104-110, customer service area 102, and the drug vaults 126 and 128, as illustrated in FIG. 2. The pharmacy computer 114 contains, or is directly linked to databases containing at least a linked list of local prescribers and identifying numbers, and a list of current prescriptions held by the pharmacy 100. In addition, the exemplary pharmacy computer 114 is connected with the remote pharmacist via a network 138.

In the exemplary embodiment, the drug retrieval vault 126 is physically connected with the drug compounding vault 128 by a pneumatic delivery tube 130, as schematically shown in FIG. 3. The drug retrieval vault 126 is also in physical connection with a customer terminal 103, an internal self-service terminal 104, a customer service area 102, a one-stop external self-service terminal 106, and an external pickup terminal 110 via pneumatic delivery tubes 129, 131, 134, 132 and 133. Although in this exemplary embodiment, the connection between a customer terminal 103 and the customer service area 102 or the drug retrieval vault 126 is direct, as can be seen in the schematic representation of the pneumatic delivery system in FIG. 3, in other embodiments the pneumatic delivery system may be configured as a web of interconnected pneumatic delivery tubes, with the customer, the remote pharmacist, or the technician controlling the transmission of items to one or more of a number of destinations. Exemplary embodiments may include pneumatic tube systems like that described in U.S. Pat. No. 6,146,057, the disclosure of which is incorporated herein by reference.

An exemplary embodiment includes one or more customer terminals 103 which permit a customer to order and receive pharmaceutical items without using the customer service area 102. The features of a particular customer terminal 103 may vary depending on a number of factors. For example, a drive-up terminal may incorporate different features than a terminal located within a store. Similarly, a customer terminal 103 that is intended to be a one-stop terminal may incorporate different features than one that is intended to accept an order for later pick-up at either a pick-up terminal or the customer service area 102. The general features that are likely to be included in an exemplary customer terminal 103 are described below.

Figure 4:
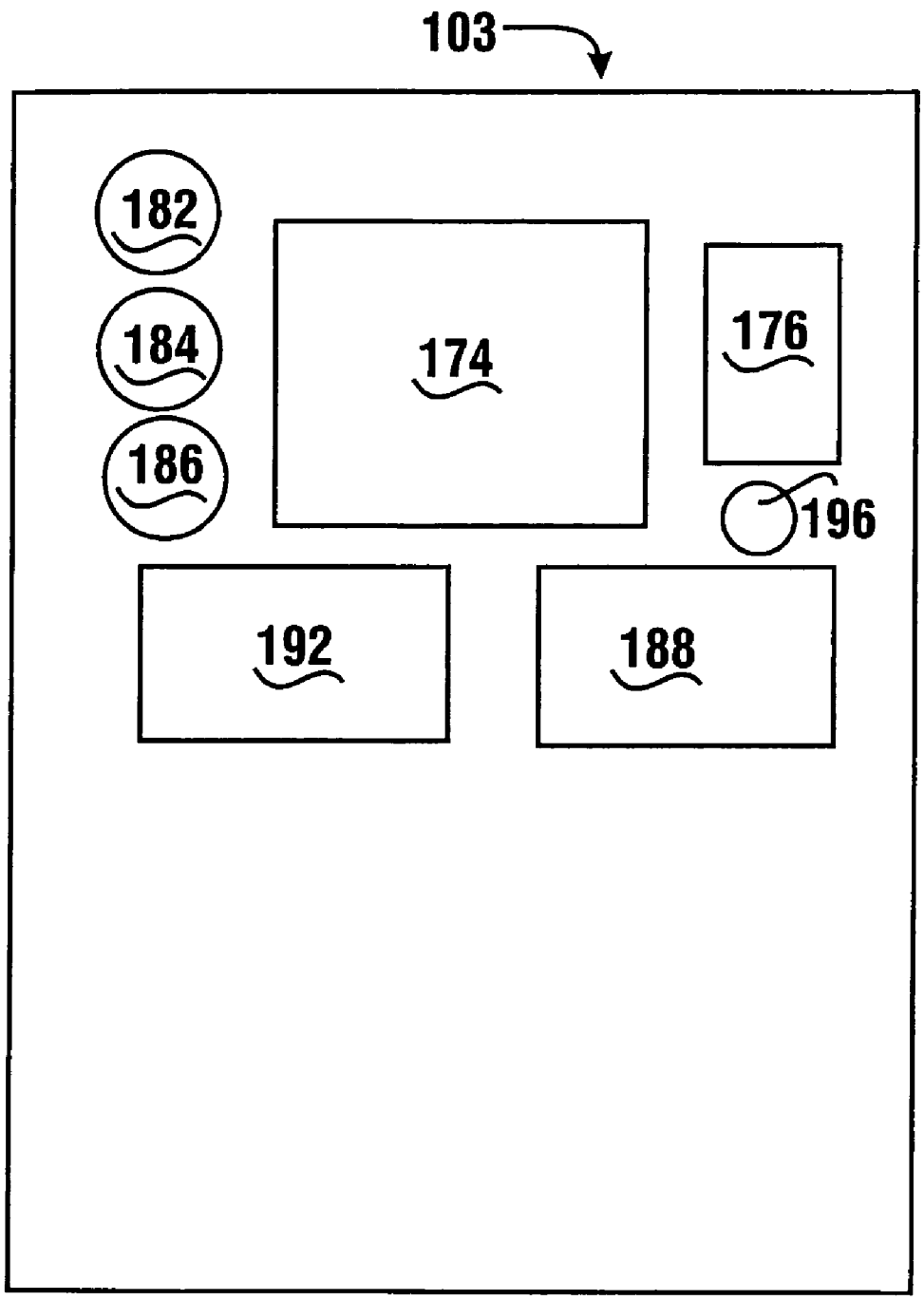
FIG. 4 is a front view of an exemplary customer terminal.

An exemplary embodiment of a customer terminal 103 is shown in more detail in FIG. 4. This exemplary embodiment of a customer terminal 103 includes a dual purpose video screen 174. The video screen 174 functions as part of a CCTV system which is in connection with a remote pharmacist. The CCTV may also be in connection with the customer service area 102. When functioning as a CCTV, the video screen 174 works in conjunction with the speaker 184, microphone 186, and CCTV camera 182 to permit interactive communication between the customer, the remote pharmacist, and the technician at the customer service area 102. It also serves as part of a computer system which permits the customer to interact with either the customer service area 102 or a remote pharmacist by using communication software, firmware, and electronic input devices such as a mouse, keyboard, keypad, or a touch screen.

The exemplary embodiment of a customer terminal 103 provides various ways to submit prescription or other order information, identified schematically as dedicated input devices 176. These dedicated input devices 176 may include, for example, a magnetic or other type of card reader, a prescription scanner, check scanner, keyboard, keypad, graffiti pad, microphone, and/or optical reader which is capable of reading bar or other information. The customer may also provide information using multipurpose devices such as a touch screen, CCTV camera, or wireless communication devices. Any method of accepting information from a customer in a format that may be transmitted from the pharmacy computer 114 to a remote location using electronic or wireless technology may be used. In other embodiments the customer terminal may include biometric reading devices such as fingerprint readers, iris scanners, facial scanners, or other devices that receive one or more identifying inputs from the customers.

This exemplary embodiment of a customer terminal 103 also permits a remote pharmacist or a technician to provide information to the customer. Information may be provided using dedicated output devices, represented schematically and identified by the reference numeral 188. Exemplary dedicated output devices 188 may include a drug information printer, a receipt printer, a speaker, and encoding devices for magnetic or optical data. Information may also be provided to the customer through multipurpose devices such as the video screen 174 and CCTV. It should be understood that any output device that is capable of transmitting information to the customer, whether in printed, electronic, magnetic, audible, visible, or other form, and whether encoded or directly accessible by the customer, may be used.

This exemplary embodiment of a customer terminal 103 also includes access to a pneumatic delivery system. Pneumatic delivery access opening 192, shown on the front of the customer terminal 103, provides access to a carrier which moves in a pneumatic delivery system which may be connected to one or both of the drug retrieval vault 126 and the customer service area 102. Although in this exemplary embodiment the connection between a customer terminal 103 and the customer service area 102 or the drug retrieval vault 126 is direct, as can be seen in the schematic representation of the pneumatic delivery tubes 129 and 139 in FIG. 3, in other embodiments the pneumatic delivery system may be configured as a web of interconnected pneumatic delivery tubes, with the customer, the remote pharmacist, or the technician controlling the transmission of items in appropriate carriers to one or more of a number of destinations within the system.

In this exemplary embodiment, the customer terminal 103 includes an alert button 196 to inform the remote pharmacist or the technician in the customer service area 102 that the customer is at a customer terminal 103. It should be understood that an alert button 196 is one of many means by which the remote pharmacist or the customer service technician may be alerted to the presence of a customer. Other embodiments may include more or different alert methods. For example, suitable alert mechanisms include, but are not limited to, proximity sensors, motion sensors, keyboards, weight sensing mats and drive over sensors.

As noted above, there are many possible configurations for customer terminals generally similar to customer terminal 103. Some likely configurations are suggested in FIG. 2. Two full service customer terminals are illustrated: an internal self-service terminal 104 and an external self-service terminal 110. It is also sometimes desirable to split the pharmaceutical delivery process by permitting orders to be placed at one terminal and picked up at another. Exemplary embodiments of partial service terminals illustrated in FIG. 2 include an external order terminal 106, and an external pick-up terminal 108. Although the embodiment illustrated in FIG. 2 suggests splitting the functions for the drive-up terminals on the exterior of the store, it may be desirable to separate the functions at the inside terminals as well. For example, a customer may wish to drop off an order for a prescription or other item at a customer terminal located near the front of a store, and pick it up at the customer service area 102 after shopping. The particular features of each customer terminal may be selected to accommodate customer demand, store policy, or legal requirements. However in general, each pharmacy 100 will likely include a full service terminal or a combination of partial service terminals which provide CCTV communication with the remote pharmacist, and means to accept a prescription or order, means to dispense a filled prescription or order, means to pay for the item ordered, and means to dispense any printed information that is required to be provided with the item ordered.

Figure 5:
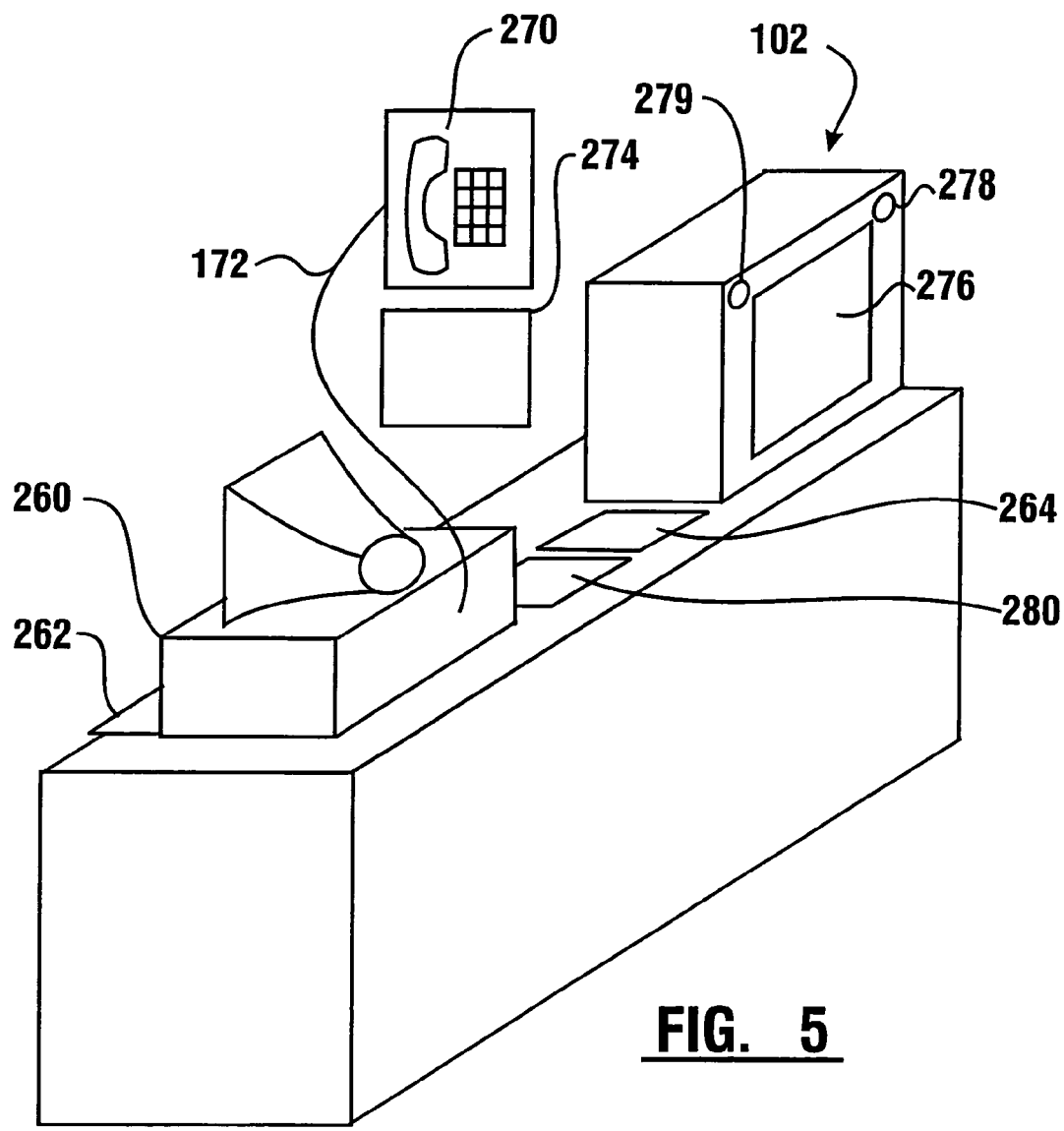
FIG. 5 is a side view of a representative customer service area.

This exemplary embodiment of a pharmacy 100 includes a customer service area 102. The customer service area 102 is represented in FIG. 5 and is generally indicated by reference numeral 102. The customer service area 102 includes a customer service terminal 260. The technician enters information into the customer service terminal 260 by using at least one input device 262, generically represented as a keyboard 261. Although in this illustration the input device 262 is depicted as a keyboard 261, in other embodiments it may include other devices which permit interactive entry of requests for pharmaceutical care into the customer service terminal 260. Such devices may include, but are not limited to, an electronic input device such as a mouse, touch screen, writing pad, or a light pen.

The exemplary customer service area 102 incorporates a customer service telephone 270. The customer service telephone 270 is connected to the customer service terminal 260, illustrated schematically and denoted by reference numeral 172. In this embodiment the customer service area 102 also incorporates a CCTV system so that the customer or the technician may speak directly with the remote pharmacist. The CCTV system is represented by the video screen 276, and includes a CCTV camera 278 and speaker 279. In addition, in this exemplary embodiment the customer service area 102 includes one or more dedicated input devices, depicted schematically and denoted by the reference numeral 264. Dedicated input devices 264 may include, but are not limited to, graffiti pads, card readers, prescription scanners, optical readers, and magnetic readers.

The customer service area 102 may also include dedicated output devices, depicted schematically and denoted by the reference numeral 280. Exemplary dedicated output devices 280 include a drug information printer, a receipt printer, a speaker, and encoding devices for magnetic, optical, or other data. Information may also be provided to the customer through multipurpose devices such as a video screen 174 or a CCTV system. It should be understood that any output device that is capable of transmitting information to the customer, whether in printed, electronic, magnetic, audible, visible, or other form, and whether encoded or directly accessible by the customer, may be used.

Finally, in this exemplary embodiment the customer service area 102 is connected to the drug retrieval vault 126 and to each of the customer terminals 103 by a pneumatic delivery system, the access opening to which is schematically depicted and referenced by the numeral 274. In this exemplary embodiment, the connections between the customer service area 102 and the customer terminals 103 or the drug retrieval vault 126 are direct, as can be seen in the schematic representation of the pneumatic delivery system in FIG. 3. It should be understood that in other embodiments the pneumatic delivery system may be configured as a web of interconnected pneumatic delivery tubes, with the customer, the remote pharmacist, or the technician controlling the transmission of items to one or more of a number of destinations in the system.

Figure 6:
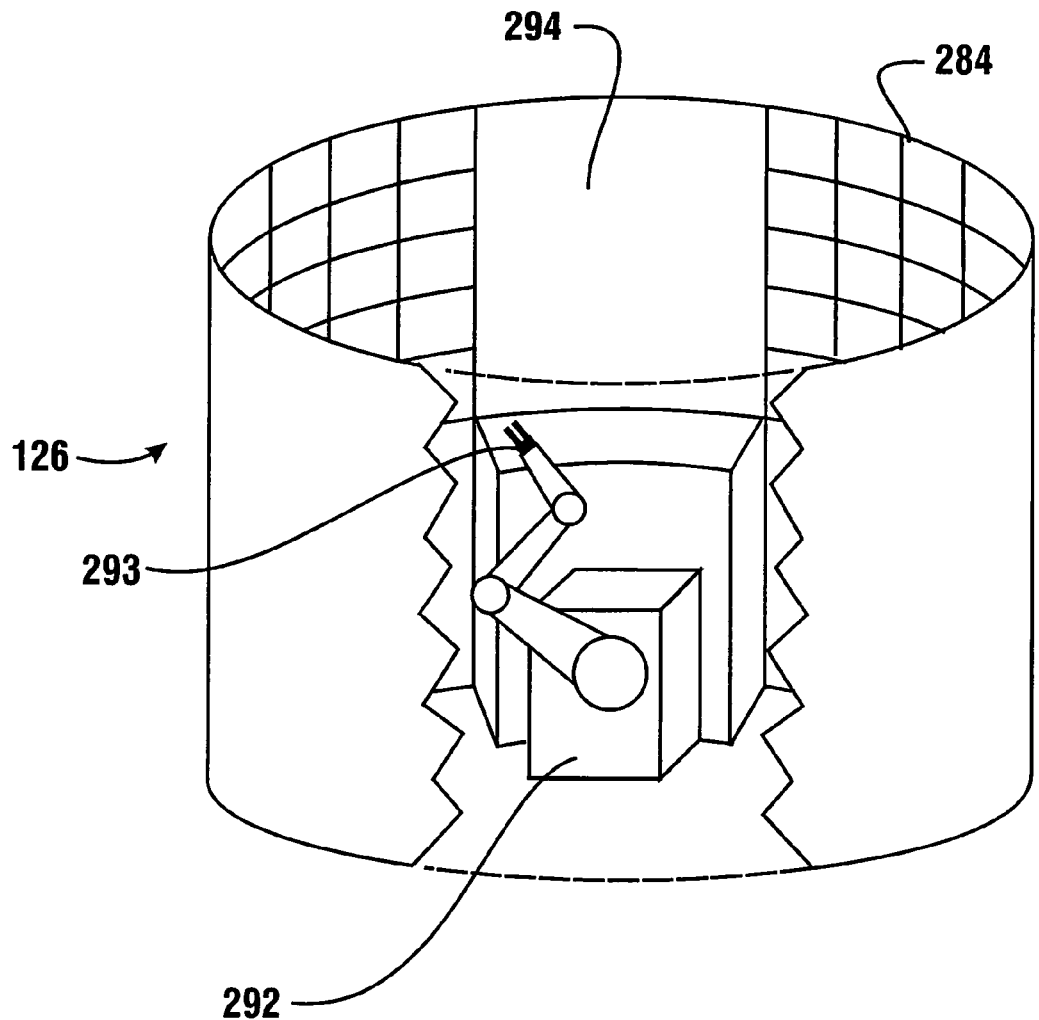
FIG. 6 is an elevated view of a drug retrieval vault.
Figure 7:
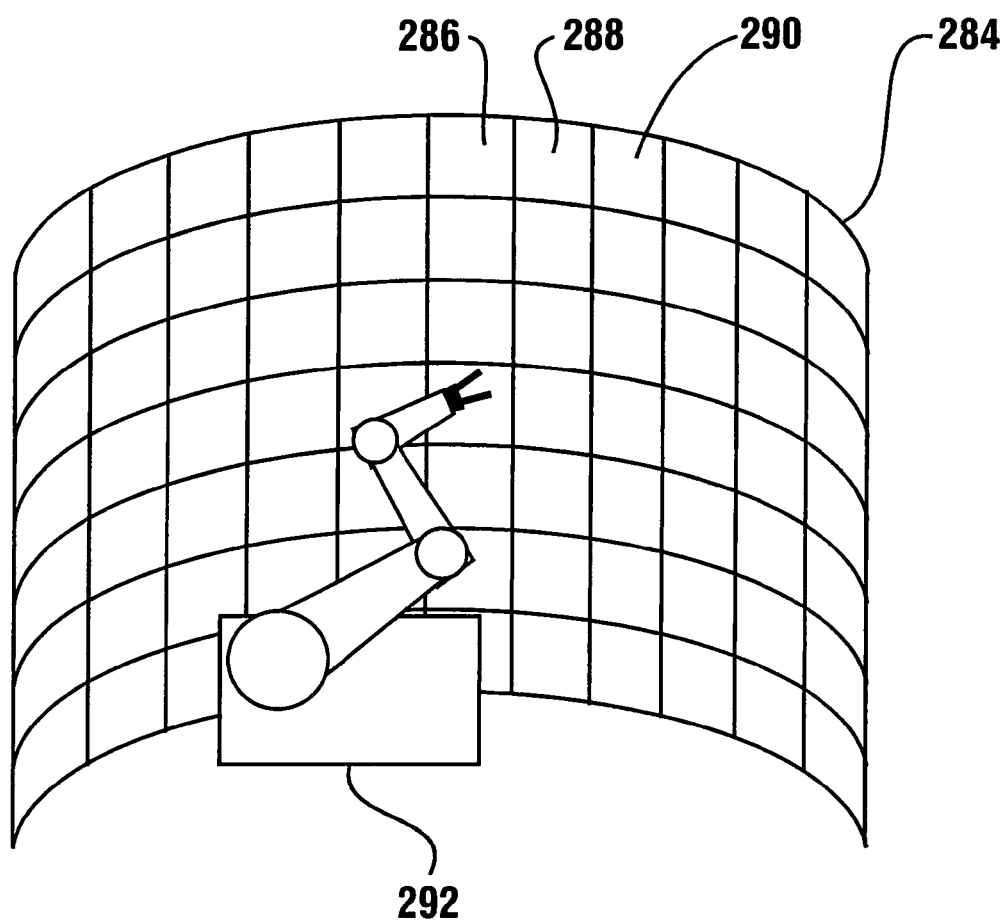
FIG. 7 is a partial cutaway view of a drug retrieval vault.

In this exemplary embodiment, preparation of pharmaceutical items may take place in two vaults, a drug retrieval vault 126 and a drug compounding vault 128. The drug retrieval vault 126 is illustrated in FIG. 6. The drug retrieval vault 126 is preferably in a secured area, accessible only to individuals who are authorized to enter it. The walls of the exemplary drug retrieval vault 126 are generally curved and incorporate a plurality of drug storage cells. In this embodiment the drug storage cells generally cover a large portion of the walls of the drug retrieval vault 126. That portion of the walls is referred to as the drug storage area 284, and is illustrated in FIG. 7. Representative individual drug storage cells are labeled 286, 288, and 290 in FIG. 7.

Prescription medications, or other items that may be ordered or needed for compounding are stored in the drug storage cells. The contents of each drug storage cell are linked in computer memory or through machine readable indicia, or both, to a unique drug storage cell location identifier, such as, for example, the x-y coordinate position of the drug storage cell, the grid position, the height and angle of rotation, or any other similarly unique identifier. The linked information is stored in a database, which is accessible to one or more of the remote pharmacist, the drug retrieval robot 292, or the technician.

Figure 8:
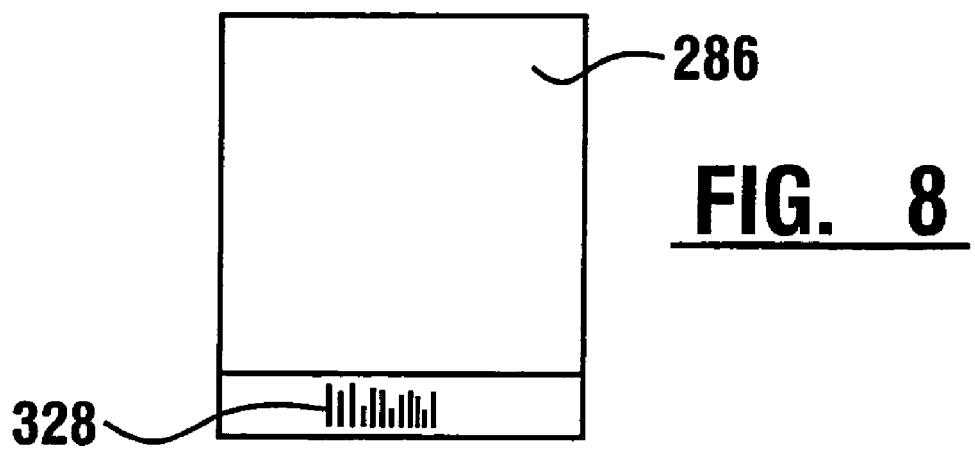
FIG. 8 is a front view of a drug storage cell.
Figure 9:
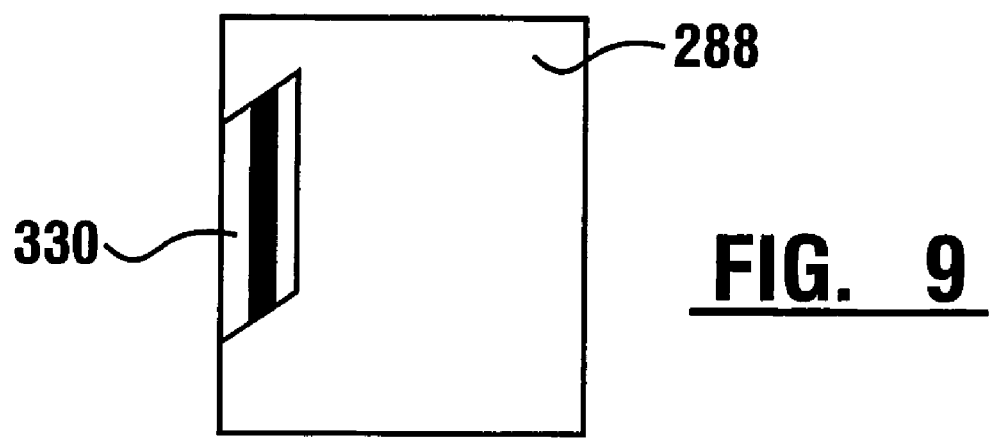
FIG. 9 is the front view of another drug storage cell.
Figure 10:
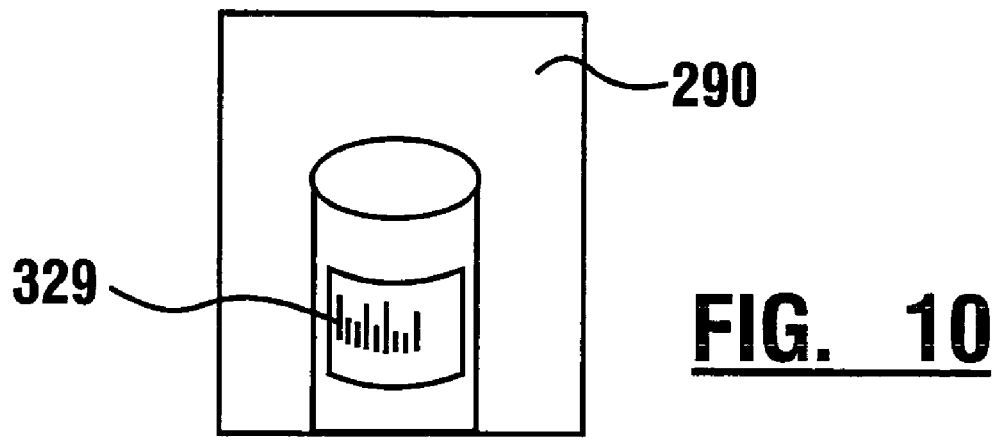
FIG. 10 is the front view of another drug storage cell which contains a bulk product.

In this exemplary embodiment additional coded information is available that may be used to verify that the contents of a particular drug storage cell match the expected contents of a particular drug storage cell. As illustrated in FIG. 8 the drug storage cell 286 contains machine readable indicia in the form of a bar code strip 328 on the front of the lower shelf of the cell 286. In FIG. 9, drug storage cell 288 contains a card with a magnetic stripe, which extends from the left side of the drug storage cell 288. In FIG. 10, the packaging of the contents of the drug storage cell 290 contains other machine readable information. In addition to information that can be used to verify the identity of the item to be dispensed, a variety of additional data may be encoded in this manner, such as packaging, inventory, drug interaction, pricing, or other information.

Figure 11:
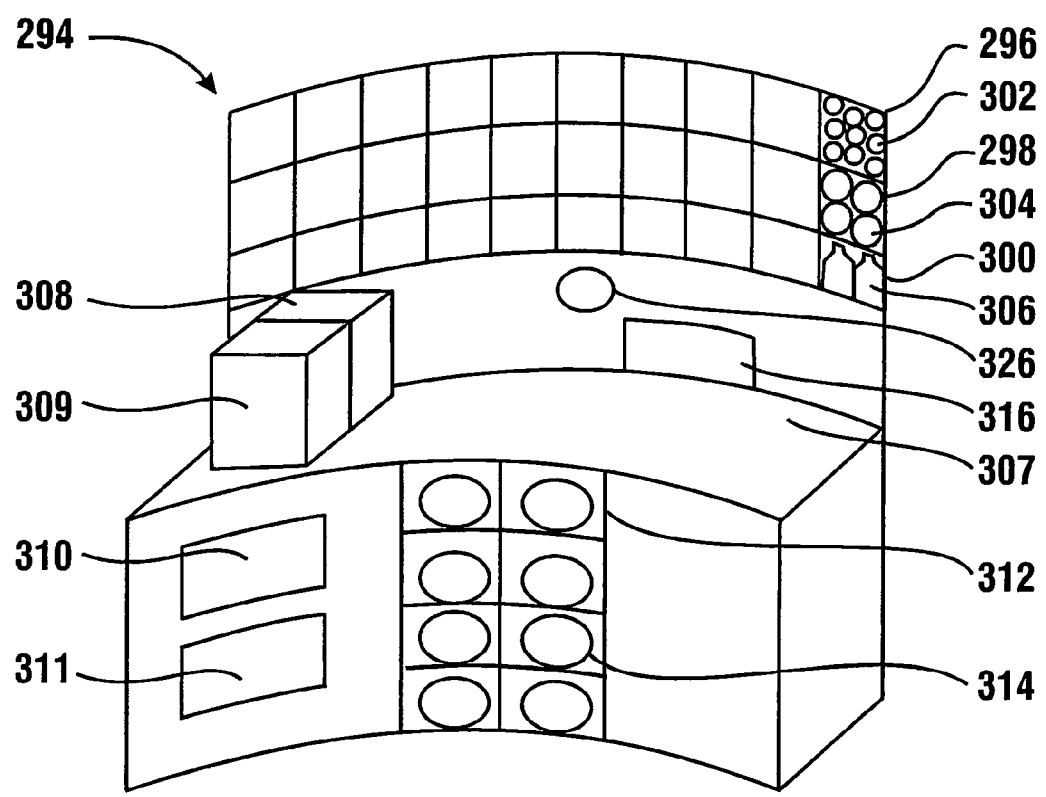
FIG. 11 is a cross-sectional view of the drug preparation area of a drug retrieval vault.

Illustrated in FIG. 11 is a different section of the wall of the exemplary drug retrieval vault 126. This section is generally referred to as the packaging wall 294. One portion of the packaging wall 294, illustrated in this embodiment as the upper portion, contains cells which hold the containers needed to package the prescriptions or items ordered by the customers. Three exemplary package cells are identified by the numerals 296, 298, and 300. Various sizes and shapes of customer packaging are shown in representative fashion and are identified by the numerals 302, 304 and 306. In addition, the exemplary packaging wall 294 contains various devices needed to quantify the pharmaceutical products requested. Shown in a representative manner on a packaging counter 307 which is attached to the packaging wall 294 are a counting device 308 and a measuring device 309. Although in this exemplary embodiment of the packaging wall 294 there are two quantifying devices, in other embodiments there may be fewer, more, or different quantifying devices. For example, a pharmacy 100 selling both pills and insulin syringes would probably not be able to use the same counting device for both. Likewise, the measuring device needed to measure an ointment would likely be different than one needed to measure a liquid. In the exemplary pharmacy 100, the drug retrieval vault 126 should contain all the measuring devices that would be needed to accurately quantify anything that is expected to be sold at the pharmacy 100.

A label printing device 310 and a drug information printer 311 are built into the exemplary packaging counter 307. In this exemplary embodiment, the packaging counter 307 also contains a storage area 312 and containers adapted to be moved within the pneumatic delivery system. Access opening 316 to the pneumatic delivery system is also located on the packaging wall 307. In this exemplary embodiment there are six pneumatic delivery tubes 130, 129, 131, 132, 133, and 134, each of which directly connects the drug retrieval vault 126 to one of the drug compounding vault 128, a customer terminal 103, and internal self-service terminal 104, a one stop external self-service terminal 106, the external pickup terminal 110, and the customer service area 102. In other embodiments the pneumatic delivery system may be configured as an interconnected web of pneumatic tubes, with the customer, the remote pharmacist, or the technician controlling the transmission of items to one or more of a number of destinations in the system. In still other embodiments, the pneumatic delivery system may be a combination of individual straight line delivery systems and an interconnected system of tubes with multiple destinations.

As shown in FIG. 6, in the center of the exemplary drug retrieval vault 126 is a drug retrieval robot 292. The drug retrieval robot 292 in this exemplary embodiment is adapted through the operation of one or more computers to perform at least some of the following: (1) receive directions from a remote pharmacist; (2) deliver information to a remote pharmacist; (3) locate a particular drug storage cell; (4) read the information encoded and attached to the cell or to the contents of the cell; (5) verify that the contents of the cell are those that were expected; (6) retrieve an item from the storage cell; (7) move selected items to the preparation area; (8) deliver selected items to the drug compounding vault 128; (9) count a specified quantity of the selected item; (10) measure a specified quantity of the selected item; (11) retrieve an appropriate container for the selected and quantified item; (12) put the selected and quantified item in the selected container; (13) retrieve prepared items from the drug compounding vault 128; (14) retrieve a label from the printer; (15) retrieve a drug information sheet from the printer; (16) place the label onto the container; (17) display the selected item and the dispensed item to the remote pharmacist via CCTV; (18) deliver the packaged item to the appropriate customer terminal or customer service area 102 via a pneumatic delivery system; (19) deliver drug information sheets to a customer terminal 103 via a pneumatic delivery system; or (20) other tasks necessary to prepare a pharmaceutical order.

The drug retrieval robot 292 is adapted to perform these tasks at the direction of a remote pharmacist. While the remote pharmacist generally directs the actions of the drug retrieval robot 292, some of the subroutines necessary to perform these tasks may be preprogrammed into computers in operative connection with the drug retrieval robot 292 so that the remote pharmacist is not required to direct the actions of the drug retrieval robot 292 in minute detail.

The exemplary drug retrieval robot 292 is equipped with a camera 293 which is connected with the CCTV system, and which may be aimed by the remote pharmacist at areas within the drug retrieval vault 126. In addition, there may be one or more cameras contained in the walls of the drug retrieval vault 126 connected with the CCTV system, which are controllable by the remote pharmacist and which permit the remote pharmacist to view activity within the drug retrieval vault 126. One such CCTV camera is located along the packaging wall, and is indicated by the reference numeral 326 in FIG. 11.

Figure 12:
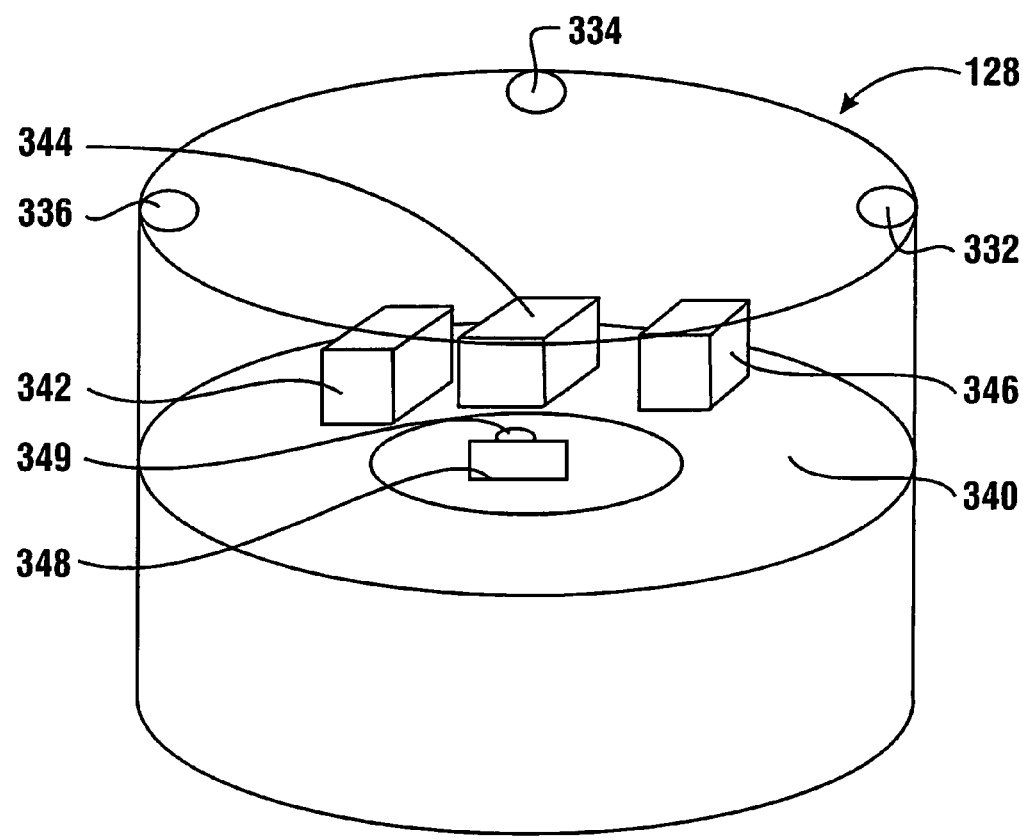
FIG. 12 is an elevated view of a drug compounding vault.

FIG. 12 illustrates an exemplary drug compounding vault 128. The drug compounding vault 128 is preferably a secured area, accessible only to individuals who are authorized to enter it. In this exemplary embodiment, a compounding shelf 340 extends horizontally inward from a portion of the wall of the drug compounding vault 128. Various compounding devices, schematically shown and indicated by reference numerals 342, 344, and 346 are located on the compounding shelf 340. In addition to the compounding devices, the compounding shelf 340 may also contain various quantifying devices, similar to those contained in a drug retrieval vault 126. The drug compounding vault 128 may also contain various packages for packaging the compounded items, similar to those contained in the drug retrieval vault 126.

A compounding robot 348, schematically represented, is situated in the drug compounding vault 128. An exemplary compounding robot 348 in a drug compounding vault 128 will be able to do one or more of the following: (1) receive communications from a remote pharmacist, including detailed directions for compounding a particular medication; (2) retrieve the individual components of a prescription from the pneumatic delivery system; (3) count a specified quantity of the selected item; (4) measure a specified quantity of the selected item; (5) retrieve an appropriate container for the selected and quantified item; (6) put the selected and quantified item in the selected container; (7) use the various compounding devices located in the compounding vault to prepare medications that require compounding; (8) display the individual ingredients to the remote pharmacist via CCTV; (9) display the compounding process to the remote pharmacist via CCTV; (10) display the completed product to the remote pharmacist via CCTV; (11) deliver the completed product to the drug preparation vault via the pneumatic delivery system or (12) other tasks necessary to compound medications.

Four CCTV cameras, three of which are shown and indicated by the reference numerals 332, 334, 336, are located near the top of the wall of the exemplary drug compounding vault 128, at positions roughly equidistant from each other. In this exemplary embodiment, the cameras 332, 334, 336 may be manipulated by the remote pharmacist in order to monitor aspects of the compounding process. A compounding robot 348 in an exemplary embodiment also contains a CCTV camera 349 that may be manipulated by the remote pharmacist to monitor the details of compounding process. It should be understood that although this exemplary embodiment includes four CCTV cameras, other embodiments may include more or fewer cameras, and the cameras may be placed in different locations than those depicted in FIG. 12.

Figure 13:
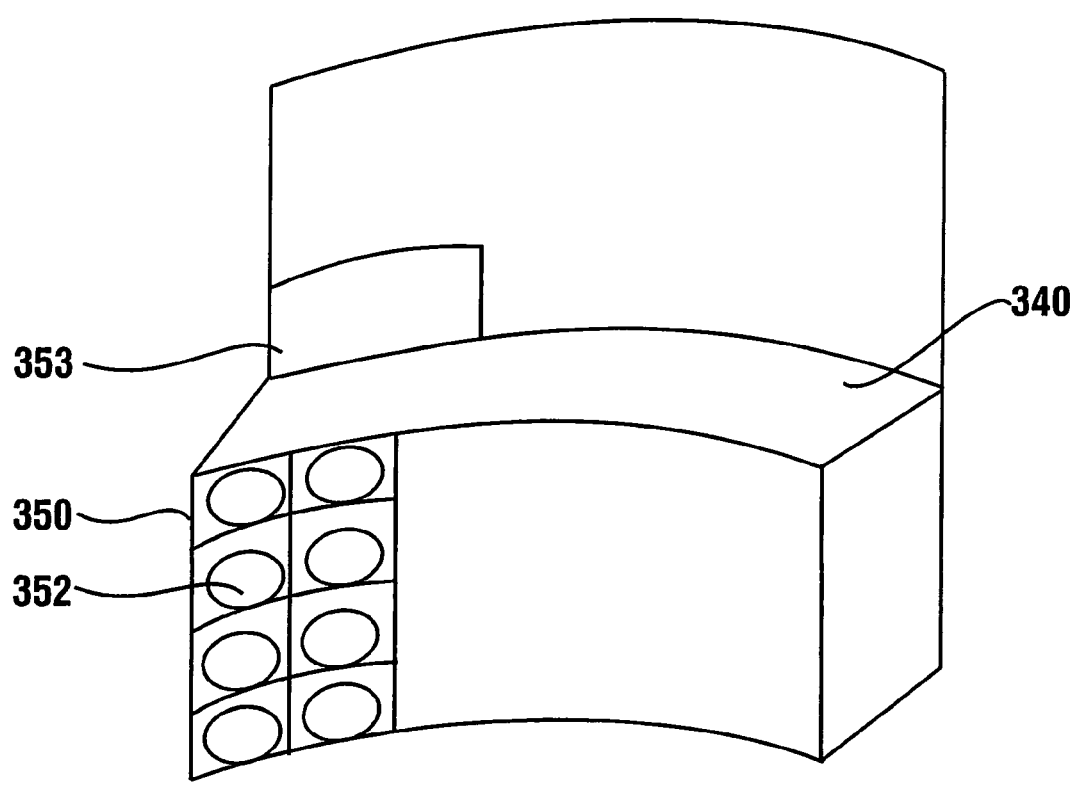
FIG. 13 is a partial cutaway view of a transmission area of a drug compounding vault.

FIG. 13 shows a cutaway portion of the drug compounding vault 128. The portion illustrated in FIG. 13 is the communication center of the drug compounding vault 128. The container storage area 350 and containers 352 adapted for placement in pneumatic carriers are located below the compounding shelf 340 in the drug compounding vault 128. Carriers may be of various types, such as for example carriers of the types shown in U.S. Pat. Nos. 5,131,792; 5,304,017; or 4,715,750, the disclosures of which are incorporated herein by reference. In this exemplary embodiment, the access opening 353 to the pneumatic delivery tube 130 is located above the compounding shelf 340. In this exemplary embodiment, the pneumatic delivery tube 130 directly connects the drug retrieval vault 126 to the drug compounding vault 128. In other embodiments, a pneumatic delivery system may be configured as an interconnected web of pneumatic tubes, with the customer, the remote pharmacist, or the technician controlling the transmission of items to one or more of a number of destinations in the system.

Although in this exemplary embodiment there are two separate vaults in which the preparation of prescriptions or other items takes place, in other embodiments there may be only one vault in which preparation occurs. A single vault may contain one, two, or more robots, or other item handling devices, and may include each of the items that are contained in one or the other of exemplary drug retrieval or compounding vaults 126 or 128. In still other embodiments, there may be more than two vaults for a particular pharmacy 100, or the components of each of two vaults may be different than the exemplary vaults described above, as may be appropriate to meet the needs of each individual pharmacy or pharmaceutical system.

The connection between the two geographically remote portions of the exemplary pharmaceutical system is now discussed. Returning to FIG. 1, in the method of operation of an exemplary embodiment, a single remote pharmacist is operatively linked to a number of individual pharmacies 96, 98, 100. In this exemplary embodiment, the remote pharmacist is remote from all of the individual pharmacies 96, 98, 100 in which he controls the operations. In other embodiments, despite the term used here, the remote pharmacist may be located in one pharmacy, for example, pharmacy 96, and operatively linked to the remaining pharmacies 98, 100 over which the remote pharmacist has authority. Although in this embodiment, the remote pharmacist is shown as operatively linked to three pharmacies 96, 98, 100, in other embodiments the remote pharmacist may be linked to fewer or more pharmacies.

There are two primary links in the exemplary system between the remote pharmacist and the individual pharmacies 96-100. One link is through the CCTV system. In an exemplary embodiment, a remote pharmacist has at least one CCTV camera 164 including audio and video communication devices, through which the remote pharmacist may communicate with customers at customer terminals 103 in each pharmacy 96-100. In this exemplary embodiment, the CCTV display uses a separate video screen 163. In other embodiments, there may be more than one video screen, or the CCTV display may appear on the pharmacist terminal 260.

A second link includes the pharmacist computer 140, which is operative to communicate with the pharmacy computer 114 through network 138. The transmission of prescription or order information, and the directions to the drug retrieval and compounding robots 292 and 348, for example, may use this link. In order to protect the integrity of the exemplary system, both the pharmacist computer 140 and the pharmacy computer 114 may utilize firewalls, encryption techniques, and/or other security measures to prevent unauthorized access. Interactions involving any customer terminal 103, the customer service terminal 260, or the drug retrieval and compounding robots 292 and 348, and an individual or computer outside the pharmacy 100, must be authorized by the pharmacy computer 114. Similarly, external interactions with any portions of the system that are controlled by the pharmacist computer 140 must be authorized by the pharmacist computer 140. The pharmacist computer 140 may also utilize a firewall, encryption techniques, and/or other security measures to prevent unauthorized access.

The remote pharmacist in the exemplary embodiment has access through the pharmacist computer 140 to various databases including, for example, a patient history database 144, a drug database 148, and a rules database 152, as shown in FIG. 1. These databases are connected to the pharmacist terminal 162 directly or through one or more wide area or local area networks 142. In addition, the pharmacist terminal 162 is also adapted to access external databases 156 through the pharmacist computer 140 and one or more networks 138. An exemplary external database is represented schematically in FIG. 1, and identified by the reference numeral 156.

In addition to being adapted to access databases, the exemplary pharmacist terminal is adapted to permit a remote pharmacist to do one or more of the following tasks: (1) interact with a pharmacy technician, (2) interact with a customer, (3) accept prescription or order and insurance information, (4) initiate the transmission of prescription or order and insurance information in the absence of a technician, (5) manipulate the drug retrieval robot 292, (6) manipulate the drug compounding robot 348, (7) manipulate the cameras in the drug retrieval and compounding vaults 126, 128, (8) control operation of printers and other dedicated output devices in the drug retrieval vault 126, customer terminal 103, and the customer service area 102 to output information that may be provided to the customer, (8) prepare a list of concerns related to a particular customer's use of the item ordered, (9) direct the display of information on multipurpose devices at a customer terminal 103 or the customer service area 102, (10) determine the price to be charged for a particular order, including adjusting for insurance payments, (11) direct the delivery of packaged products through the pneumatic delivery system, and (12) other tasks necessary to the remote operation of an automated local pharmacy.

Figure 14:
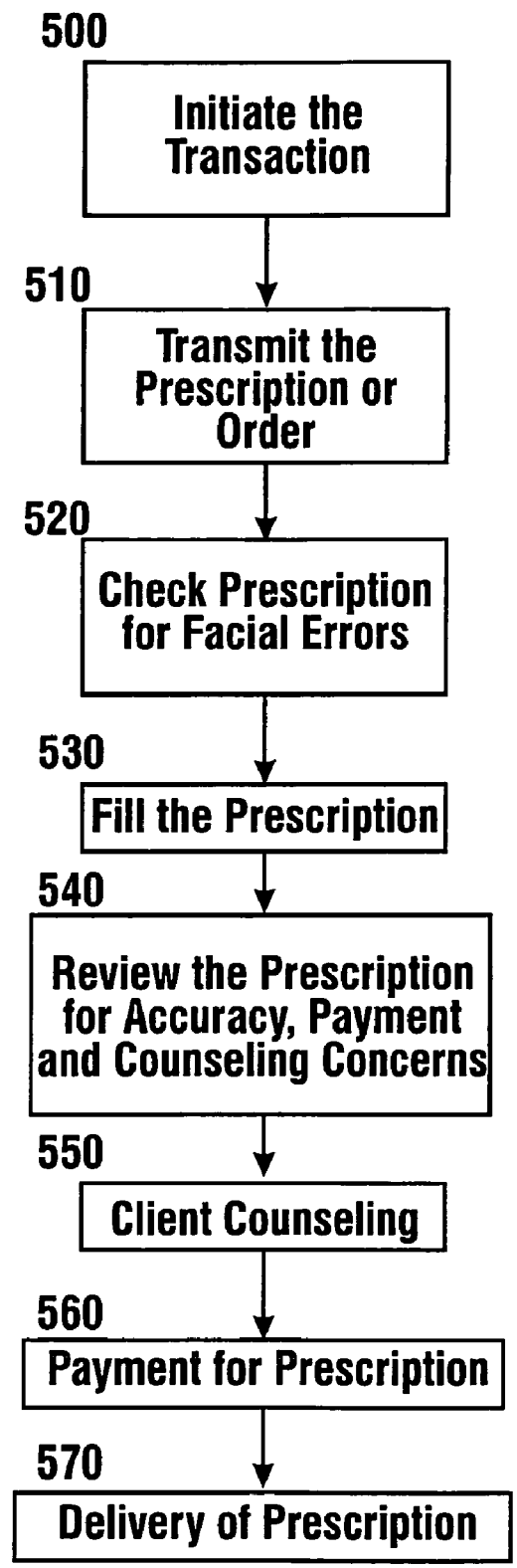
FIGS. 14 through 16 are flow charts representing a method operating a pharmaceutical system of this invention.

FIG. 14 schematically represents an overview of an exemplary transaction flow used in processing a prescription in the exemplary pharmacy system previously described. Initially, the prescription is presented to a local pharmacy 100 and transmitted to a remote pharmacist, as indicated in steps 500 and 510. Once the prescription is received by a remote pharmacist, it is initially reviewed for facial accuracy, and steps are taken to resolve any facial errors, as indicated in step 520. As noted in step 530, the remote pharmacist then fills the prescription. This is done by directing the drug retrieval robot and compounding robots 292 and 348 in the local pharmacy 100 where the order originated to prepare the prescription. In this exemplary embodiment, as represented in a step 540, once the prescription is prepared, additional checks are performed to ensure that the prescription was accurately filled, to guide patient counseling, and to accurately price the prescription. Following this second review of the prescription, the remote pharmacist may offer to counsel the customer, payment is made, and the medication or other item is delivered, as represented in steps 550-570.

With minor variations, the same steps may be followed for the purchase of a non-prescription item which is required to be distributed through the pharmacy. Examples of such items include cough medication containing small amounts of narcotics, insulin syringes, or other items that do not necessarily require a prescription but may be subject to abuse. It should be understood that any reference to a prescription includes other items, the distribution of which must be made through the pharmacy.

Figure 15:
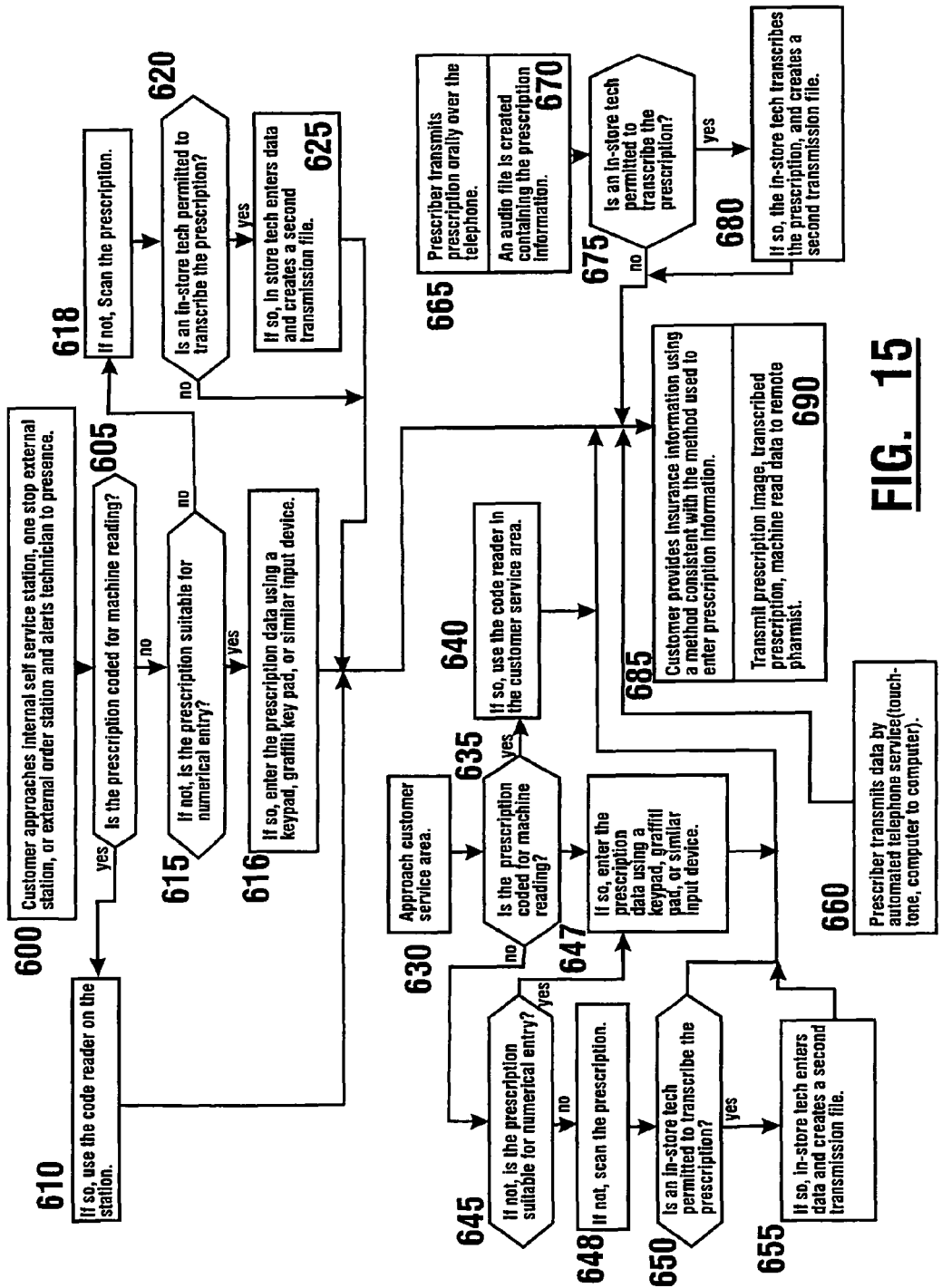

The initiation of the transaction and the transmission of the prescription to the remote pharmacist, steps 500 and 510 in FIG. 14, are illustrated in more detail in FIG. 15. In an exemplary embodiment there are four ways to initiate a request for a pharmaceutical or other item. These are represented beginning with steps 600, 630, 660, and 665 respectively. Steps 600 through 625 represent what occurs if a customer uses a customer terminal 103 to present a prescription, or other order, to the remote pharmacist.

Steps 630 through 655 describe the process followed if the customer presents the prescription directly to a technician staffing the customer service area 102. Step 660 represents the direct transmission of a prescription or order to the pharmacy 100 by an automated means. Finally, steps 665 through 680 describe the transmission of a prescription to a technician over the telephone by a prescriber 170.

Returning now to the first method for transmitting the prescription, as described in steps 600 through 625. In this embodiment the customer places the order by means of a customer terminal 103. The customer terminal 103 may be internal or external, and may be a full service terminal or a terminal adapted to accept orders for pickup at another location.

As represented in a step 600 in FIG. 15, the customer approaches the customer terminal 103 and alerts the technician in the customer service area 102 by pressing the alert button. Although in this exemplary embodiment the technician is alerted by means of an alert button 196, it should be understood that any number of suitable alert mechanisms may be used, some of which are described above.

After alerting the technician that a customer is waiting, the customer will present the prescription to the technician. How the presentation is presented will depend on the form of the prescription. The prescription will likely be in one of three forms. It may be in an encoded form suitable for machine reading, in numerical form suitable for keypad entry, or handwritten. Suitable formats for machine reading would include bar coding, optical characters, or magnetic coding. As represented in steps 605 and 610, if the prescription is coded for machine reading the customer is directed to use the appropriate reader on the customer terminal 103 for reading machine readable indicia. Once read, the prescription data is electronically transmitted to the technician.

If the prescription is not in a format suitable for machine reading, it may be in a format suitable for keypad entry, as represented in a step 615. A prescription refill is one example of a request for pharmaceutical care that is generally in numerical format and is suitable for keypad entry. Such prescriptions may be entered using a keypad or graffiti pad, represented in step 615. Once entered, the prescription data is electronically transmitted to the technician.

Finally, the prescription may not be coded for machine reading, and may not be suitable for keypad entry. Most handwritten prescriptions fit this category. If the prescription is of this nature, indicated by a negative response to both of the queries in steps 605 and 615, the customer scans the prescription or other order using the prescription scanner 178, as indicated in a step 618. The image of the prescription is electronically transmitted to the technician. In some instances a technician may be permitted to transcribe the prescription, in others a pharmacist may be required to do the transcription as determined in a step 620. If a technician is permitted to transcribe the prescription, as is represented in a step 625, the technician will enter the data from the image into an electronic form presented on the pharmacy computer 114. If the technician is permitted to transcribe the prescription, the technician will send both the transcribed file, and the file containing the scanned prescription image to the remote pharmacist, otherwise the technician will transmit only the image file to the remote pharmacist.

Another exemplary method of initiating the transaction is for the customer to go to the customer service area 102 in the store, as represented in a step 630. As previously described, the customer service area 102 is adapted to accept a prescription or order in any of the formats acceptable for the mechanical prescription transmission discussed above. If the prescription is coded for machine reading, determined in a step 635, the customer or the technician uses the appropriate reader at the customer service area 102 to create a file containing the order, as represented at step 640. If the prescription consists of information that may be entered using a keypad, determined in a step 645, the customer or technician enters the prescription data using a keypad or graffiti pad, described in a step 640. On the other hand, if the prescription is not suitable for either machine reading or keypad entry, the prescription is scanned to create an image file, as represented in a step 645. If a technician is permitted to transcribe the prescription, as determined in a step 650, then a technician also enters the data into a facsimile form in the customer service terminal 260, and creates both an image file and a data file.

In addition to a customer bringing a prescription to a pharmacy 100 it is also customary for pharmacies to accept prescriptions directly from a prescriber 170. In an exemplary embodiment, a prescriber 170 may transmit the data directly to the customer service terminal 260 by a semi-automated means, such as using the touch tone buttons on the telephone, as represented in a step 660. A prescriber 170 may also, or alternatively, transmit a data file over telecommunication lines from the prescriber's computer 171 to the customer service terminal 260.

In addition, a prescriber 170 may use a more traditional means of transmitting the prescription, such as verbally relaying the information to the technician over the telephone, as represented in steps 665-680. The technician will create an audio file, which may be either analog or a digital, in a format that can be sent to the remote pharmacist, as represented in a step 670. In some instances, a technician may be permitted to transcribe the prescription or order information. If so, as determined in a step 675, the technician transcribes the information into a format that can be transmitted to the remote pharmacist, and prepares a second file for transmission to the remote pharmacist, as represented in a step 680. This may be accomplished, for example, by entering the data into a facsimile form presented on a customer service terminal 260.

In addition to transmitting prescription data, a customer may also transmit insurance information by any of the means described above that is adapted to accept the format in which the insurance information is presented, as represented in a step 685. Once the prescription or order information and any insurance information has reached the customer service terminal 260, the technician may transmit the prescription and insurance information to the remote pharmacist through the pharmacy computer 114 over a network 138, as represented in a step 690. In some cases, as indicated in steps 655, 625, and 675, the technician may reformat the information and create a prescription facsimile data file to be transmitted to the remote pharmacist along with the audio or visual image file of the prescription and the insurance information. In some embodiments the insurance information may be routed to another computer or service provider that can validate and/or process payments based on the insurance information.

Although in the exemplary embodiment, the prescription or order information is presented first to a technician at the customer service area 102, in some embodiments there may not be a technician present in the pharmacy 100, or the technician may be occupied with other tasks. If the order is being placed by a customer at a customer terminal 103 without the intervention of a technician, the remote pharmacist will be alerted to the initial presence of the customer. When the customer transmits information from the customer terminal 103 to the customer service terminal 260, the remote pharmacist will access the customer service terminal 260 over the network 138 through the pharmacy computer 114 and cause the transmission of the order and insurance information from the customer service terminal 260 to the pharmacist terminal 162.

If the order is being placed by a prescriber 170 over the telephone or by an electronic transmission without the intervention of a technician, the customer service terminal 260 may verify with the pharmacy computer 114 that the prescriber 170 is an authorized prescriber. This may be done using various techniques such as passwords, digital signatures, or other suitable verification techniques. Once the prescriber 170 is verified as an authorized prescriber, the customer service terminal 260 may accept the prescription or order and prepare it for transmission to the remote pharmacist. Similarly, if no technician is available and a customer telephones a request for a refill of a prescription, the pharmacy computer 114 may verify that the prescription is valid, that there are remaining refills, and that the prescription has not expired. If so, it may accept the prescription or order and prepare it for transmission to the remote pharmacist.

When the customer service terminal 260 has received data corresponding to a valid prescription, it may notify the remote pharmacist, by using the pharmacy computer 114 to transmit a message to the pharmacist computer 140 over the network 138. The remote pharmacist may then authorize the customer service terminal 260 to transmit the prescription file or files to the pharmacist terminal 162.

The mechanism by which an order reaches a remote pharmacist without the intervention of a technician may vary from the description above. A desirable feature, however, includes verification by a gatekeeper, such as the pharmacy computer 114 or a pharmacist computer 140, that the prescription is authorized by an individual who is permitted to write prescriptions or, if a refill, that the prescription on file is still valid.

Turning in more detail to an exemplary procedure followed by the remote pharmacist, initially the remote pharmacist verifies whether there are facial errors in the prescription which might prevent it from being filled, represented in a step 520 in FIG. 14. Facial errors are those apparent from the face of the prescription. Examples of this kind of error include a prescription that is missing information that is required by law, a prescription which orders an amount of medication that does not match the instructions for using it, or one that is missing a prescriber's name, or one that appears to have been tampered with, for example. If there are facial errors in the prescription, the remote pharmacist follows the pharmacy or state mandated policy and/or organizational policy to correct those errors or to reject the prescription or order. Although in this exemplary embodiment, any facial errors in the prescription are discovered and corrected as a preliminary step, in other embodiments some of the verification of facial accuracy may be delayed until the second review of the prescription, represented in a step 540 in FIG. 14, as long as the prescription or order contains enough information to determine which item is being ordered and what quantity is to be dispensed. In still other embodiments, this initial review may be more extensive, and may include some of the reviews described as being performed during the second review.

Once the prescription is in condition to be filled, the remote pharmacist provides inputs operative to cause the connected computers to direct robots 292 and 348 in the two drug vaults 126 and 128 to prepare the prescription for the customer. An exemplary form of this process is represented schematically in FIG. 16. The remote pharmacist must initially decide whether filling the prescription will involve only the drug retrieval robot 292, or both the drug retrieval and the compounding robot 348. This decision is represented in a step 800. If the prescription or order requests something which is pre-packaged or which may be selected and quantified, the remote pharmacist will send instructions to the drug retrieval robot 292 to obtain the item and to prepare it for delivery to the customer. This process is represented in steps 810 through 865.

The group of items that may be prepared solely by the drug retrieval robot 292 in the exemplary embodiment are divisible into two categories. One category comprises those items that are prepackaged for delivery. Antibiotic packs and tubes of ointment, for example, are often prepackaged for sale. The other category of the items that can be prepared solely by the drug retrieval robot 292, are those that are not yet packaged for delivery. Whether the items are prepackaged or need to be quantified, the initial steps are the same, and are represented in steps 810-825 in FIG. 16.

The remote pharmacist directs the drug retrieval robot 292 to retrieve the desired item by directing it to the drug storage cell containing that item, as represented in a step 810. The location of the drug storage cell may be determined with reference to a data file which contains information linking a particular item to a particular drug storage cell. The identification of the drug storage cell may be done by the remote pharmacist, with the remote pharmacist directing the drug retrieval robot 292 to the identified location. In the alternative, the remote pharmacist may direct the drug retrieval robot 292 to retrieve a particular item, relying on locating subroutines that have been preprogrammed into a computer linked to the drug retrieval robot 292 to determine the specific location of the requested item. Once the item is retrieved, the drug retrieval robot 292 is directed to verify that the item retrieved is the item requested, as represented in a step 820. This verification may be accomplished by comparing the information encoded on the drug storage cell or on the packaging of the selected item with the data file containing the linked content and location information.

At this point, the item may be ready for labeling, as determined in a step 825. On the other hand, if the item needs to be measured or counted, additional steps, including those represented in steps 835-850, must be performed before the order is ready to be labeled. If quantification is required, once the item has been retrieved and its identification verified the remote pharmacist operates or directs the drug retrieval robot 292 to measure or count the medication. If the item ordered requires counting, as determined in a step 830, the remote pharmacist directs the drug retrieval robot 292 to use the appropriate counting device 308, and to count the number of pills or objects to be dispensed, as represented in a step 835. If the medication is a liquid or a powder, and needs to be measured instead of counted, the remote pharmacist directs the drug retrieval robot 292 to use the appropriate measuring device 309 to measure the correct quantity to be dispensed, as represented in a step 840.

Once the item has been measured or counted, the remote pharmacist directs the drug retrieval robot 292 to select an appropriate package, based on the nature and quantity of the item ordered, represented in a step 845. The remote pharmacist may select the appropriate package, and direct the drug retrieval robot 292 to retrieve it. In the alternative, the remote pharmacist may direct the drug retrieval robot 292 to use packaging information to select and retrieve the proper package. Packaging information may be stored in the bar code, magnetic code, RFID tag or other indicia attached to the drug retrieval cell or to the bulk package associated with the ordered item. Although in this exemplary embodiment, the remote pharmacist 161 directs the drug retrieval robot 292 in the package selection process, in other embodiments a computer linked to the drug retrieval robot 292 may be programmed with subroutines to perform part or all of this task automatically, once a particular item and quantity have been requested by the remote pharmacist.

After the package is selected and the item ordered is quantified, the remote pharmacist directs the drug retrieval robot 292 to dispense the quantified item into the selected package and to seal the package, as represented by a step 850. Although in this exemplary embodiment, the remote pharmacist directs the packaging process, in other embodiments part or all of the process may be carried out using preprogrammed subroutines resident in a computer linked to the drug retrieval robot 292.

Figure 16:
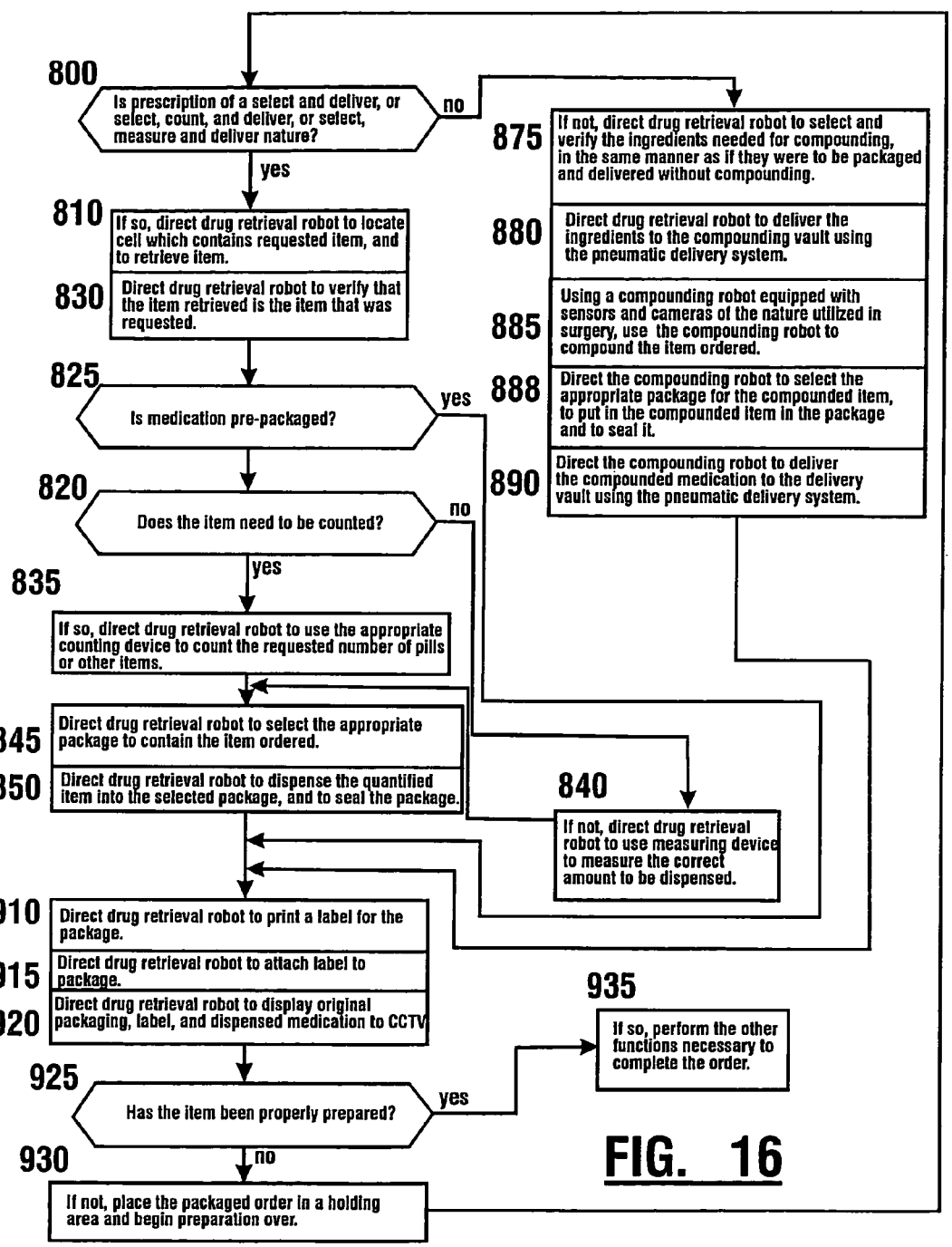

As represented in FIG. 16, steps 875-890, there are some medications that require more preparation than selecting, or selecting and quantifying. In that event the remote pharmacist directs the drug retrieval robot 292 to retrieve the appropriate components to produce the medication requested and to deliver them to the drug compounding vault 128 using a carrier transmitted through the pneumatic delivery tube 130, as represented in steps 875 and 880. The carrier is opened through actions of the compounding robot. Each component is selected and its identification verified in the manner described above. Once the components have arrived at the drug compounding vault 128 the remote pharmacist directs the motions of the compounding robot 348 to compound the requested item, as represented in a step 885. The remote pharmacists uses the network 138 and remote control devices, such as virtual reality glasses and tactile input devices, or similarly sophisticated software and devices to control the movements of the compounding robot 348.

In a manner similar to that described above, the pharmacist directs the compounding robot 348 to measure each item when it is needed, and to use the compounding tools available to mix the items together to form the medication ordered.

In this exemplary embodiment the drug retrieval robot 292 selects each bulk package that contains an ingredient that is needed and transmits it to the compounding robot 348. The compounding robot then measures the raw ingredients and compounds the medication. In other embodiments, the remote pharmacist may direct the drug retrieval robot 292 to measure the ingredients, and to send only the quantity required by the drug compounding robot 348 for compounding. Of course in other embodiments other approaches may be used.

In the exemplary embodiment, after using the compounding robot 348 to prepare the requested medication, the remote pharmacist directs the compounding robot 348 to select an appropriate package, to put the compounded medication in the selected package, as represented by a step 888, and to return the compounded medication to the drug retrieval vault 126, represented by a step 890. In this exemplary embodiment, the compounding robot 348 selects and retrieves the package for the compounded product. In other embodiments, the drug retrieval robot 292 may select the appropriate package and send it to the compounding robot using the pneumatic delivery tube 130.

Returning to the exemplary overall process, once the medication is packaged for delivery to the customer, whether it was prepackaged, required counting, required measuring or compounding, it may be labeled. The remote pharmacist directs the label printer 310 to print an appropriate label for item ordered, represented as a step 910. The drug retrieval robot 292 is then directed to attach the label to the package, as indicated in a step 915. The remote pharmacist may also direct the drug information printer 311 to print the appropriate drug information sheet for the medication prepared.

In this exemplary embodiment the tasks necessary to prepare prescriptions or other orders are split between two separate vaults, and performed in part by each of two separate robots. In other embodiments all of these tasks may be performed by a single robot in a single vault. In further embodiments, these tasks may be split differently, or may be accomplished in more than two vaults or by more than a single robot in each of one or more vaults.

The next step in the exemplary embodiment is for the remote pharmacist to verify that the medication is ready to be delivered to the customer. After the package is labeled, the remote pharmacist directs the drug retrieval robot 292 to position the original packaging and the labeled medication or other item so that the label is visible to the remote pharmacist via CCTV camera 326, or another appropriate camera, as represented in a step 920. In an exemplary embodiment the pharmacist terminal 162 may display a split screen. One side of the screen may contain the image of the prescription as it was transmitted to the remote pharmacist. If both a prescription image and a facsimile generated from encoded or transcribed data are available, both may be displayed. If the prescription was ordered verbally, the remote pharmacist may also play the audio file or a computer generated text version or other record of the audio file.

The other half of the screen may include one or more images from the drug retrieval vault 126, including the original packaging of the item being dispensed and the product that is packaged for delivery to the customer. The remote pharmacist may use these images and audio files to verify that any transcription of a prescription or order is accurate, and that the medication being dispensed to the customer is the medication that was prescribed for that customer, as represented by a step 925.

Although in this exemplary embodiment, a split screen is used to display both the request and the product that was packaged in response to that request, the verification may be performed in other ways such that it generally includes (1) comparing any transcription to the audio or visual image of the original prescription or order and (2) comparing the order to the packaged product. It should also be understood that verifying the accuracy of any transcription may alternatively be done during the earlier review, represented as a step 520 in FIG. 14, rather than during the second review, represented as a step 540 in FIG. 14.

If the remote pharmacist has any concerns about whether the packaged product matches the prescription or order, the remote pharmacist in the exemplary embodiment may retrieve additional information to verify the accuracy of the prepared product. The remote pharmacist has access to the prescription transmission data, data from the bar code or the magnetic strip of the drug storage cell, data that was encoded on the packaging of the item selected from a particular cell, the link data identifying the item that should have been in a particular drug storage cell, a video recording of the compounding process, and visual images from the selection and compounding process as captured by the CCTV cameras. In addition, the remote pharmacist has the ability to direct the drug retrieval robot 292 to manipulate the packaging or to point cameras, contained in the drug retrieval and compounding robots 292 and 348, or in the walls of the drug retrieval and compounding vaults 126, 128, at selected drug storage cells or anything else within the drug retrieval vault 126 or the drug compounding vault 128. Finally, the drug database 148 that is linked to the pharmacist terminal 162 contains images of the medications and other items that may be prescribed or ordered. The remote pharmacist can also direct the drug retrieval robot 292 to open the prepared package so that the contents can be compared to the image of the item that should have been dispensed.

If the concerns cannot be resolved, the remote pharmacist may direct the drug retrieval robot 292 to place the medication in a holding area for appropriate disposal or restocking at a later time, and to refill the prescription, as represented in a step 930 in FIG. 16.

Once the prepared product matches the written prescription or order, the remote pharmacist may perform additional reviews, and other tasks necessary to prepare the ordered item for delivery to the customer, as represented in a step 935. In this exemplary embodiment the remote pharmacist compares the prescription or order to various resident databases 148 and 152, or external databases 156 to verify that the physician is correctly identified, and that the dosage dispensed is within the suggested dosage range for that particular medication. If the remote pharmacist discovers a discrepancy, the remote pharmacist follows a preestablished policy or procedure to correct the discrepancy.

The exemplary pharmacist computer 140 also compares the prescription or order to the individual patient history in the patient database 144 to reveal any potential drug interactions or allergies that may indicate the customer should use caution or avoid using the medication or item ordered. In addition, the pharmacist computer 140 may be linked through a network 138 to external databases 156 which may also have records for this particular patient. In that event, the pharmacist computer 140 performs a similar search and comparison in those external databases 156. If this comparison reveals contraindications, the remote pharmacist follows the preestablished policy to address those concerns.

In addition in the exemplary embodiment the pharmacist's computer 140 compares the prescription to the customer's medical plan, contained in the rules database 152, to determine if generic substitutions are permitted, whether the medication prescribed is in the formulary for the patient's health plan, and any applicable co-pays. If any of these inquiries raise concerns, the remote pharmacist follows the preestablished policy to address those concerns.

Although in this exemplary embodiment, this second review is done after the prescription is filled, in other embodiments it may be done before the prescription is filled in order to avoid restocking prescriptions if, for example, the customer might choose not to fill a prescription for a medication that is not part if the insurance company's formulary, or might choose to purchase a generic substitute instead of a more expensive named product. Much of this verification may be automated in some embodiments, and can also occur while the prescription or order is being prepared.

Before delivering the medication or other item to the customer, the remote pharmacist may offer to counsel the customer about the item ordered, represented in a step 550 in FIG. 14. In this exemplary embodiment the pharmacist computer 140 is programmed to generate a limited list of concerns using the information acquired during the review process. The list of concerns might include drug interactions, allergies, side effects, or insurance questions. The remote pharmacist reviews the list, selects the concerns that should be shared with the customer, and electronically transmits those concerns over the network 138 to the patient. The concerns are displayed on the video monitor 174 or 276 to the customer, along with an offer to counsel the patient. If the customer wishes to speak with the remote pharmacist, an interactive consultation takes place via an audiovisual link through the CCTV located in customer terminals 103 or at the customer service area 102 to which the customer has access.

Although in this exemplary embodiment, the remote pharmacist uses the video monitor 174 or 276 to transmit concerns to the patient, the concerns could also be transmitted to the customer in printed format using one of the output devices at a customer terminal 103 or the customer service station 102. In addition, although the remote pharmacist may make counseling available to the customer immediately via CCTV, the remote pharmacist may also offer to provide counseling over the telephone after the customer has returned home and has had a chance to review any printed information he or she received. In that event, the remote pharmacist will provide a telephone number to the customer for his or her later use.

Following this consultation, the prescription is paid for and the product is delivered to the customer, represented in a step 560. In the exemplary embodiment at the customer terminal 103, the cost of the prescription may be displayed on the monitor. The customer may select a method of payment via the touch screen option. If the customer wishes to pay by a credit or a debit card, a customer may use the card reader at the customer terminal 103 and follow the automated procedure to authorize payment. Access to the credit or debit processing locations 120 and 118 is obtained through the pharmacy computer 114. In the alternative, if the customer wishes to pay by cash or check, the customer uses a carrier transmitted in the pneumatic delivery tube 139 to send the cash or a check to the technician in the customer service area 103. A pharmacy 100 may also use a check scanner, so that payment by check may be made by passing a check through a check scanner, which is connected to an electronic debit processing location 120 through the pharmacy computer 114.

If payment is made at the customer service area 102, the technician processes the payment by normal commercial means. In the exemplary embodiment once the payment has been processed, the drug delivery robot 262 is directed to deliver the prescription to the customer via the pneumatic delivery tube 274. The technician, or a remote pharmacist, directs a drug information sheet to be printed at the customer terminal 103 or the customer service area 102. In addition, the remote pharmacist directs any other information that must be provided to the customer to be printed at the customer terminal 103 or the customer service area 102. Although in this embodiment, the drug information sheet is printed at the pick-up location for the filled prescription, in other embodiments, the drug information sheet or other information may be printed in the drug retrieval vault 126, and sent to the customer through the pneumatic delivery tubes 129 or 134. In still other embodiments it may be provided to the customer in a format other than a printed page. For example, if the customer has the capability to read magnetically or electronically encoded information, the information may be encoded on a magnetic or smart card for the customer. Similarly, if the customer has access to the Internet, the remote pharmacist may provide the customer with an access code to an Internet site, having the information, rather than provide the information in printed form.

Although the procedures above are described as occurring in a particular order, the individual tasks may be performed in another order that is desirable for a particular pharmaceutical system 50 or pharmacy 100, as long as the tasks may logically be done in that order. For example, it may be desirable to perform all of the steps necessary to provide a price to the customer before the prescription or order is prepared, if prescriptions are frequently rejected in pharmacy 100 because of the cost. The steps may even be selectively performed out of order based on the nature of the item ordered. For example, it may be desirable for the remote pharmacist to survey both the resident databases 144, 148, 152 and external databases 156 when a customer orders a drug that is commonly sold illegally, in order to determine if this particular customer has ordered the medication recently from this or another pharmacy.

Many of the tasks assigned to the technician or the remote pharmacist are described as being done or performed by them. This description is intended to include the performance of tasks, or portions of tasks, by automated means which do not necessarily require the individual's conscious attention to the task. For example, the remote pharmacist is described as searching various databases during the second review of the prescription. This description is intended to include searches that are performed using preprogrammed routines, even those that may be automatically triggered when the pharmacist terminal 162 receives a transmitted prescription request. It is also intended to include manual searches of those same databases that are consciously undertaken and directly performed by the remote pharmacist.

Finally, the location of the remote pharmacist is not explicitly described because the remote pharmacist may work from any location which can support the electronic equipment required to perform the tasks described above. As suggested above, this site could be one of the pharmacies served. In the alternative, it could be the residence of the remote pharmacist, or it could be a central building from which several remote pharmacists serve. A group of pharmacies could also be served from more than one location, switching from service by one location to service by another from time to time. The location of the remote pharmacist is relatively unlimited, aside from the requirement that the location be electronically accessible and capable of supporting a computer, databases, phone lines, CCTV, and any other electronics necessary to perform the tasks above.

Figure 17:
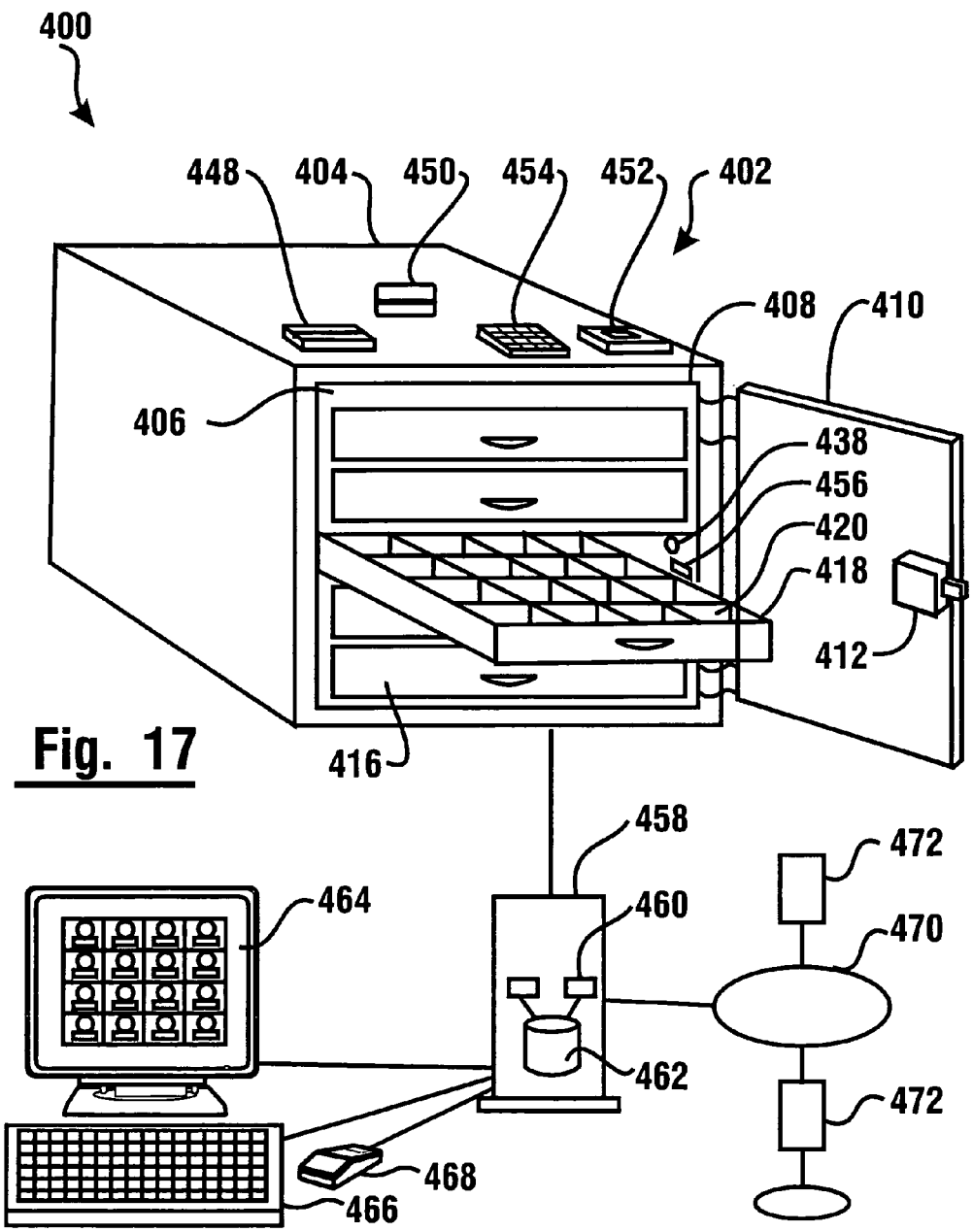
FIG. 17 is a schematic view showing an exemplary system for tracking the taking and return of narcotics items.

FIG. 17 shows an exemplary embodiment of a system that may be used in connection with tracking inventories of narcotics items or other items generally indicated 400. The exemplary system includes one or more narcotics holding vaults 402. Vault 402 includes a housing 404 which bounds an interior area 406. The interior area 406 is accessible through an opening in the housing 408. A door 410 is movably mounted in operative supported connection with the housing. The door 410 is mounted to the housing with hinges or other appropriate structures which enable the door to move between an open position shown in FIG. 17 and a closed position in which the door closes the opening 408 and renders the interior area inaccessible from outside of the housing.

In the exemplary embodiment the door is in operative connection with a lock 412. Lock 412 of the exemplary embodiment is an electrically actuated lock that is changeable between locked and unlocked conditions. When the door 410 is closed and the lock is in the locked position, the lock serves to hold the door closed. Of course in other embodiments other types of locks and securing arrangements for the door may be used.

Figure 19:
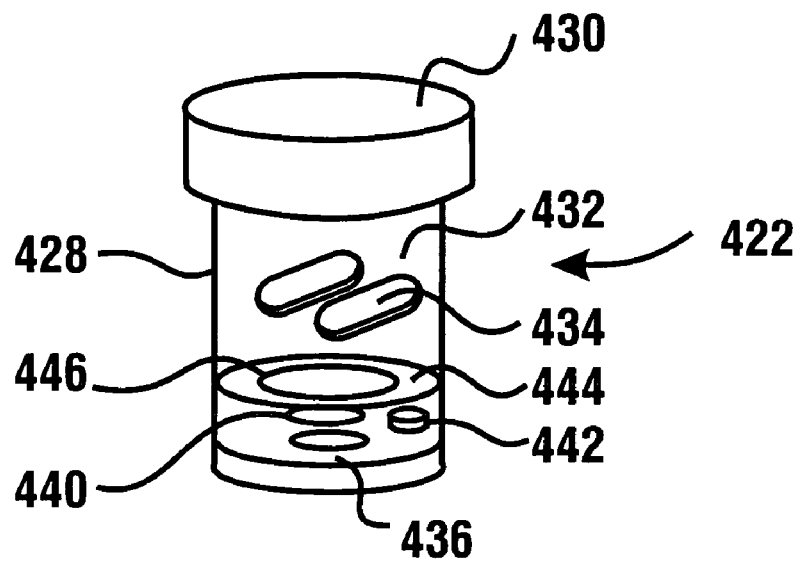
FIG. 19 is a schematic view of an exemplary narcotic item holding container.

In the exemplary embodiment the housing includes a plurality of holders 416. In the exemplary embodiment the holders are drawers which are movably mounted in supporting connection with the interior of the housing. Such mounting may be accomplished through slides, tracks or other appropriate mounting structures. In the exemplary embodiment the holders include drawers which can be extended outward through the opening 408 when the door 410 is in the open position. This is shown by an extended drawer 418 in FIG. 17. In the exemplary embodiment each holder includes a plurality of storage locations 420. In the exemplary embodiment each storage location is configured to hold a narcotic item holding container. In the exemplary embodiment the narcotic item holding container includes a vial 422 shown in FIG. 19 which is later described in detail. Of course it should be understood that in other embodiments other types of narcotic item holding containers may be used. Also in the exemplary embodiment each storage location 420 is configured to hold one narcotics holding container. It should be understood that in other exemplary embodiments storage locations may be configured to hold multiple containers that each hold a quantity of one or more narcotic or other items. Further in other exemplary embodiments other arrangements may be used.

Figure 18:
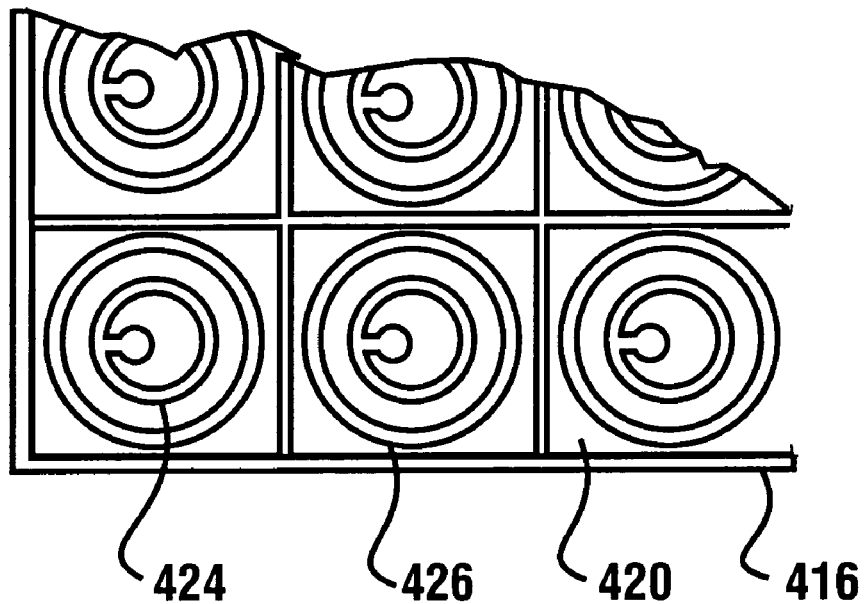
FIG. 18 is a partial view of a drawer adapted for holding narcotic item holding containers.

FIG. 18 shows a portion of a drawer of an exemplary embodiment for holding the narcotic item holding containers. Each storage location includes a reader 424. In the exemplary embodiment the reader 424 is adapted to sense radio frequency (RF) signals which are generated by RF transmitter devices included on narcotic item holding containers when positioned in the respective storage location. For example in some exemplary embodiments the RF reader devices may be operative to read RF signals which are output by RFID tags or other RF transmitter devices on narcotics holding containers that are adjacent to the reader devices as a result of being positioned in the storage locations. As can be appreciated, in exemplary embodiments the RF readers are configured to receive RF signals of sufficient strength and in the designated frequency range only from a holding container positioned in the respective storage location and not from containers that are positioned in other storage locations in the holder or in other holders. Of course this approach is exemplary and in other embodiments other approaches may be used.

Further in the exemplary embodiment of the holders 416 each storage location includes an RF programming output device 426. The exemplary RF programming output device is operative to provide signals that program programmable memories in the narcotics holding containers when they are positioned in the respective storage location. This may include for example, an output device that programs programmable RFID tags which may be included on respective narcotics holding containers. As can be appreciated, in the exemplary embodiment the respective RF programming output devices in a given storage location are operative only to program the programmable memories on containers positioned in the respective storage location, and not other containers positioned in other storage locations. Further it should be understood that in some exemplary embodiments the RF reader and RF programming output device may be combined as a single device that is in the storage location. Further it should be understood that while in the exemplary embodiment shown each of the storage locations includes a respective RF reader and RF programming output device, other embodiments may include such devices that are operative to program and read data from narcotics holding containers in a plurality of different storage locations.

In the exemplary embodiment the narcotics holding containers include vials 422. The exemplary containers include a body 428 which is releasibly engageable with a cap 430. The cap 430 can be removed to provide access to an interior area 432 of the vial. The interior area is operative to hold one or more narcotic items schematically represented 434. Although in the exemplary embodiment the narcotics holding containers comprise a cylindrical vial, it should be understood that in other embodiments other types of containers having different shapes, properties, features, material properties, closure arrangements and the like may be used.

In the exemplary embodiment the narcotics holding container includes an RF transmitter schematically indicated 436. In the exemplary embodiment the RF transmitter is operative to transmit at least one RF signal. The RF signal in the exemplary embodiment is operative to identify the container for the narcotic items held therein. In an exemplary embodiment the RF transmitter may include a radio frequency identification (RFID) tag which is operative to generate RF signals in response to an RF signal source. Such an RF signal source is represented schematically in FIG. 17 by an emitter 438. The emitter 438 may operate to produce radiation which causes the RF transmitters to provide RF signals based on backscatter principles. Of course these approaches are exemplary and in other embodiments other approaches may be used.

In the exemplary embodiment of the container 422, the container includes an RF receiver 440. The RF receiver of the exemplary embodiment is operative to receive signals from the RF programming output devices 426. The signals received by the RF receiver are used in the exemplary embodiment to program a programmable memory included on the container and schematically indicated 442. In exemplary embodiments the programmable memory 442 may be associated with a programmable RFID tag. Alternatively in other embodiments the programmable memory may be associated with a processor which has an RF interface, such as for example a Memory Spot™ device provided by Hewlett Packard. Of course these approaches are exemplary and in other embodiments other approaches may be used.

Further in the exemplary vial, a wall 444 bounding the interior area 432 includes one or more weight sensors 446. The weight sensors 446 may be of any suitable type such as sensors which have variable resistance responsive to deformation of a deformable membrane or other suitable type that can indicate the weight or mass properties of narcotics items held within the interior area of the container. Alternatively suitable weight sensors may determine the weight of the vial and/or its content by vibration or other properties. In the exemplary embodiment the weight sensor is operative to detect the weight of narcotic materials and to facilitate the use of such narcotic materials when the containers are removed and replaced in the holding areas. In the exemplary embodiment the weight sensors are in operative connection with the RF transmitter. The RF transmitter is operative to include in the RF signals that are output data corresponding to the weight currently sensed through operation of the weight sensor. Of course this approach is exemplary and in other embodiments other approaches may be used.

As shown in FIG. 17 the exemplary system includes one or more identifier (ID) record readers that are operative to receive inputs that can identify users of the system. Such identifier readers included in the exemplary embodiment include a card reader 448. Card reader 448 is operative to read user cards, such as a magnetic stripe cards schematically indicated 450. Other identifier (ID) record readers included in the exemplary embodiment include a biometric reader 452. Biometric reader 452 of the exemplary embodiment is operative to read items which include biometric features such as a user's fingerprint or finger veins. Other identifier readers may include a RFID tag reader which is operative to read RFID tags or tokens including user identifying data. In addition exemplary embodiments may include a keypad or other input devices as schematically indicated 454. Of course these identifier (ID) record readers are exemplary and in other embodiments other types may be used.

In the exemplary embodiment the drawers 416 may be selectively extended outward from the housing when the door 410 is in the open position. Suitable position sensors schematically indicated 456 are operative to sense when a respective drawer is moved to extend in the opening. The drawer position sensors operate in a manner later discussed to facilitate operation of the system by users thereof as well as to provide the capabilities for facilitating the tracking of narcotics items. Position sensors may include mechanical contact type sensors, photo sensors or other suitable sensor types.

It should also be understood that while in the exemplary embodiment of the narcotics holding vault 402, the holding locations are configured for manual access by a technician, other embodiments may be configured for use by automated systems such as the robots previously described. Further while the systems described relate to authorized user access in connection with individuals, other embodiments may provide authorized access to mechanical devices or systems.

In the exemplary embodiment of the system 400, the narcotics holding vault 402 is in operative connection with one or more computers 458. Computer 458 includes at least one processor 460 which is in operative connection with one or more data stores 462. It should be understood that while only one computer is shown, alternative embodiments may include numerous computers and networks.

In the exemplary embodiment the at least one processor 460 is in operative connection with a display 464. The at least one processor is also in operative connection with user input devices such as a keyboard 466 and a mouse 468. Of course these input and output devices are exemplary and in other embodiments other types of input and output devices may be used.

Further in the exemplary embodiment the at least one processor 460 is in operative connection with one or more networks schematically indicated 470. Network 470 is in operative connection with other computers indicated 472. Such other computers may themselves enable communication through other connected networks. As a result other exemplary embodiments may provide for the computer 458 to be in communication in numerous other systems, including systems which enable monitoring by remote pharmacist or other persons, of activities related to the taking and replacement of narcotics. Such other systems may also include systems which provide prescription data concerning the prescriptions currently being fulfilled through operation of the system. This enables the computer of the exemplary embodiment to review the current prescription data and to determine for example, that the items being removed from the narcotics vault are consistent with the nature of the prescriptions currently being prepared. Further in exemplary embodiments other connected systems may be operative to provide monitoring and tracking of narcotics items used for purposes of legal compliance. Further such tracking may also facilitate inventory management and restocking of the system. Of course these approaches are exemplary and in other embodiments other approaches may be used.

Figure 20:
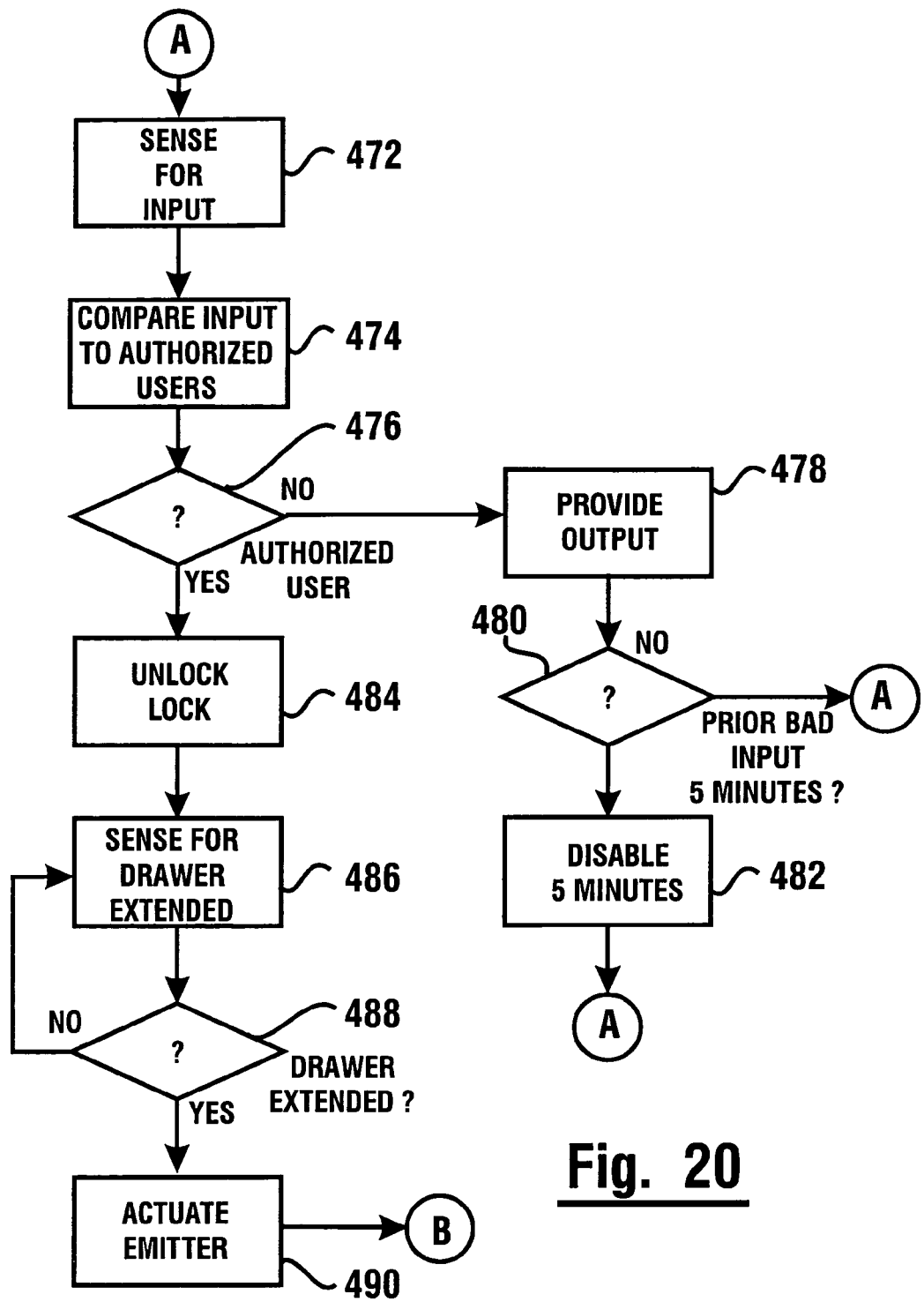
FIGS. 20 and 21 are a simplified flowchart showing logic executed by at least one processor in connection with an exemplary embodiment.
Figure 21:
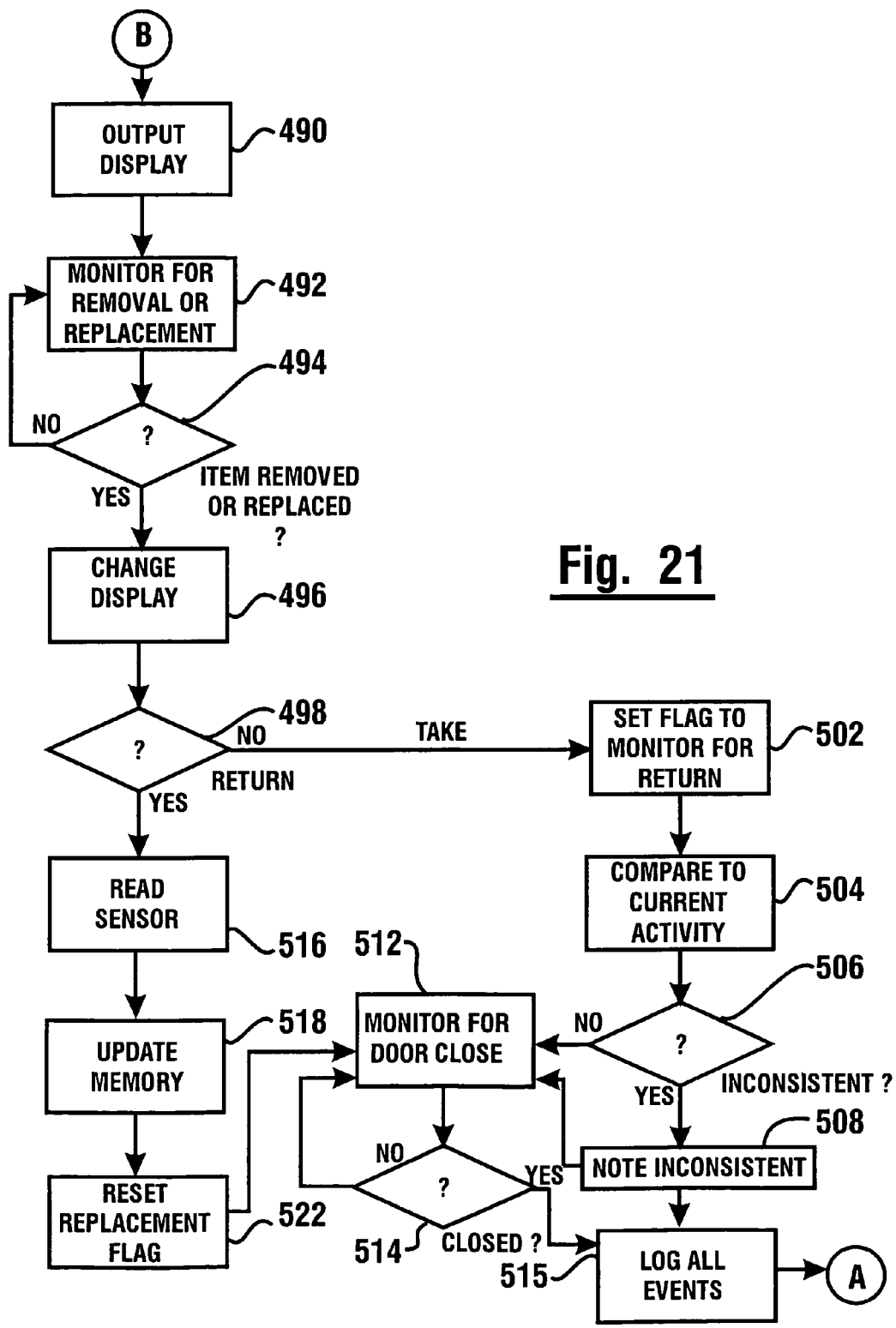

FIGS. 20 and 21 describe schematically an exemplary method of operation of the system 400. This method of operation is associated with accessing of the narcotic items in the vault by individual users. In the exemplary embodiment the at least one data store 462 includes data corresponding to a plurality of authorized users. This may include for example, data corresponding to inputs that are provided by the ID reader devices associated with or assigned to persons who are authorized to operate the system and remove narcotic items from the narcotics vault.

Further in exemplary embodiments the at least one data store includes data corresponding to the RF signals output by each respective RF transmitter on each narcotics holding container. Further in the exemplary embodiment, the at least one data store includes data corresponding to narcotics stored in the housing. This enables the system to determine what narcotics are taken and returned, as containers are removed from holding areas so the narcotics items can be taken therefrom and then subsequently returned to holding areas in the housing.

The steps represented in FIGS. 20 and 21 are associated with computer executable instructions that may be carried out through operation of the at least one processor 460 in one or more computers 458. Such computer executable instructions may be carried out in software of various types and which may be written in a variety of programming languages and architectures as may be suitable for the particular type of computer architecture involved in the particular system. Various types of software architectures and approaches may be used in connection with systems of the type described.

In operation of an exemplary system the at least one processor 460 operates in an initial step 472 to sense for inputs through one of the identifying record readers. This can be an input through a card reader like card reader 448, a biometric reader like biometric reader 452, an RFID reader or other identifying record reader connected in the system. Of course as can be appreciated, one or more types of identifying record readers may be used in various embodiments. Further additional inputs for purposes of identifying authorized users such as inputs through the keypad 454 may be received. In response to receiving such identifying inputs the at least one processor is operative to compare the input to the data stored in the at least one data store 462 to determine if the input corresponds to an authorized user. This is represented in a step 474. In a step 476 the at least one processor operates to determine if the inputs received correspond to an authorized user. If the inputs do not correspond to an authorized user, an output is provided through the display 464 indicating that access to the system is not authorized. This is represented in a step 478. In addition in the exemplary embodiment if a prior unauthorized attempt to access the system has been made in the last five minutes, the system operates to determine that such an attempt is made. This is represented in a step 480. As can be appreciated, the at least one processor 460 operates at least one timing function to determine the time of various events which occur in connection with the system. In the exemplary embodiment this timing function is operative in step 480 to determine the time when a prior unauthorized attempt to access the system was made. As indicated if such an attempt was made within the last five minutes, the exemplary system operates to disable access to the system for a five minute period. This is represented in a step 482. If no such prior attempt at unauthorized access was made during the past five minutes the computer returns to the logic flow which enables a further immediate attempt to access the system. Of course this approach is exemplary.

If in step 476 it is determined that the input corresponds to an authorized user, the at least one processor is operative to cause a lock 412 to change from the locked to the unlocked condition. This is represented in a step 484. Further as can be appreciated the at least one computer logs in the data store that the particular authorized user has accessed the system at a particular time and caused the door allowing access to the interior area of the vault to be unlocked.

The at least one processor then operates in a step 486 to sense whether a drawer 416 is extended through the opening 408. In the exemplary embodiment such an extension of the drawer is sensed by sensor 456. Sensor 456 can be any of a plurality of contact or noncontact sensors that are operative to sense when the drawer is extended such that the storage locations therein can be accessed. Further as can be appreciated, the exemplary embodiment includes the drawers 416 which are configured so that access to the storage locations therein can only be achieved when the drawers are extended through the opening. This enables the system to know when possible access to a storage location in a given drawer has been achieved. Of course this approach is exemplary and in other embodiments other approaches may be used.

If a drawer is extended this is sensed and signals to the at least one processor are provided in a step 488. In the exemplary embodiment when a drawer is sensed as being extended, the at least one processor causes the emitter 438 to operate to emit RF signals. This is represented in a step 490. As can be appreciated, in the exemplary embodiment the RF signals emitted are operative to cause the RF transmitters included on the narcotics item holding containers to produce one or more RF signals. This is done in the exemplary embodiment based on the use of RF energy being delivered from the emitter which causes the output of the RF signals from the RF transmitters 436. Of course these approaches are exemplary.

As can be appreciated the RF transmitters of the exemplary embodiment are operative to output at least one RF signal that identifies the container and/or the narcotic item contained therein. Further in the exemplary embodiment the RF signals may include weight data sensed through operation of the weight sensors. Further in exemplary embodiments RF signals may include data that is stored in the programmable memory of the narcotics holding container. In some exemplary embodiments the data stored in the programmable memory may be accessed responsive to signals received by the RF receiver which are operative to cause the output of such data encoded in the output RF signals. Exemplary embodiments may include in the programmable memory, information regarding the narcotic type containing therein, authorized users who have removed the narcotics holding containers from holding locations, the time and date data when narcotics holding containers have been removed from and returned to storage locations, the particular storage locations to which the narcotics holding containers have been taken from and returned at various times, patient data corresponding to patients for which narcotics items have been removed from a container, the weights or other quantity data corresponding to items removed from the containers at various times, as well as other data. Of course these items of data are exemplary and in other embodiments other types of data may be stored and used.

Referring again specifically to FIG. 21, in the exemplary embodiment when a drawer 416 is extended from the housing and such extension is sensed through operation of the sensor 456, the at least one computer is operative to cause the display 464 to provide at least one output. In the exemplary embodiment this at least one output includes holder indicia. Such holder indicia includes the narcotics items in each storage location in the extended drawer. This can include for example, a graphical representation of the narcotics holding containers as well as the particular narcotic items included therein. Further it should be understood that while in the exemplary embodiment graphic representations of the storage locations are shown, other approaches may include other forms of representations, including textual data and matrices of text, graphics, icons or other outputs that are usable to indicate the presence of narcotics holding containers and/or the content thereof. Such an output is represented in FIG. 21 by a step 490.

In the exemplary embodiment, with a drawer extended the at least one processor monitors for a change in conditions which corresponds to removal or replacement of a narcotics holding container in a storage location. This is represented in a step 492. As can be appreciated, when a narcotics holding container is removed from a respective storage location, the at least one RF signal provided by the RF transmitter on the removed container will no longer be sensed by the respective RF reader in the storage location. Likewise if a narcotics holding container is being returned to a storage location this will result in an RF reader reading an RF signal from the container when it is placed therein. Such changes are sensed through operation of the at least one processor and such a change is identified as represented in a step 494.

In an exemplary embodiment when a narcotics item holding container is sensed as being removed or placed in a storage location, the holder indicia output through the display 464 changes to correspond to the particular event. This may include for example a visual representation of the particular item disappearing from the output of the display screen in the area represented by the particular storage location when the item is removed. Likewise an item that is returned will appear with its associated data in the storage location as represented on the screen. Of course such events are also recorded through operation of the at least one processor, and data corresponding thereto stored in the at least one data store. Step 496 is representative of the changes in the outputs through the display caused by the at least one processor responsive to storage containers being removed from or placed in storage locations in the extended drawer.

The at least one processor determines whether a narcotics item holding container has been removed or returned as represented in a step 498. If a narcotics item has been taken, the at least one processor operates to note the event and also sets a flag to monitor for the return of the narcotic item holding container by the particular user. This is represented in a step 502. Further in the exemplary embodiment, the at least one processor is in operative communication with the at least one computer which monitors the particular prescriptions being filled at the pharmacy. The at least one processor operates in accordance with its programming to determine if the removal of the particular narcotic item is consistent with the prescriptions then currently being filled. This is represented in a step 504. A decision is made in a step 506 whether the removal of the item is inconsistent with current activity and if so, the data associated with such inconsistent activity is stored in the at least one data store 462. This is represented in a step 508. In the exemplary embodiment, the data recorded includes the data associated with the removal including the user involved, the time and date, the particular item which is being removed and the like. This data is stored so that it can later be analyzed to determine if any improper activity has occurred. Alternatively such activity may immediately be noted and an alarm or other signal provided to appropriate individuals or systems such that, for example, visual surveillance may be commenced or recorded or other appropriate actions promptly taken. Of course these approaches are exemplary.

In step 506 the at least one processor is operative to monitor for the user to close the door 410 on the narcotics vault. Such monitoring is represented in a step 512. It should be understood that in this exemplary embodiment the vault is set up such that the user is expected to engage in only one removal or return transaction each time the door is opened. In other exemplary embodiments the system may be configured so as to enable a user to engage in multiple removal and/or return transactions during one session when the door is open. This may be accomplished through the appropriate programming associated with the at least one processor 460.

In the exemplary embodiment, one or more sensors are associated with the door 410 such that the at least one processor can determine when the door is closed or open. Further in the exemplary embodiment closing of the door causes the lock 412 to automatically lock. In the exemplary transaction when an item has been taken and the door is then sensed as closed, this event is noted as represented in a step 514. The at least one processor 460 then operates to log all events associated with the taking of the narcotic item in the at least one data store of the system. This is represented in a step 514.

Alternatively in step 498 if the transaction which has occurred is a return of a narcotics holding container, the at least one processor operates to read the data provided by the RF transmitter on the returned narcotics holding container. In the exemplary embodiment this includes an indication of the particular container and/or the narcotic items included therein. This may also include in some embodiments, weight information indicative of the weight and/or quantity of the remaining items included in the container. Further in an exemplary embodiment this may also include signals concerning other data that has been stored in the programmable memory associated with the container. Of course these items of data which are included in the exemplary RF signals are only examples of information that may be provided by some embodiments. The reading of such information is represented schematically by the step 516.

As schematically represented in a step 518, the at least one processor operates in accordance with its programming to operate the RF programming output device in the particular storage location in which the container has been placed. The at least one processor operates to communicate with the RF receiver of the exemplary container to update the information included in the programmable memory. This may include for example, updating the information in the memory with data representative of the user who removed the container, the time it was removed from a storage location and returned to a storage location, the identity of the storage locations involved, the patient for which the narcotic items were taken, changes in quantity of items stored in the container based on changes in weight or other information and other data as may be stored in the programmable memory. Of course as can be appreciated the at least one processor of the exemplary embodiment is also operative to update the data stored in the associated memory 462 of the computer 458.

Further in response to sensing the return of a narcotic item holding container, the at least one processor is also operative to reset the corresponding flag set in memory when the container was removed. This is represented by a step 522. Further in the exemplary embodiment the at least one processor is also operative to review the data stored in the at least one data store 462 related to the taking of the container to verify whether any abnormal conditions are associated with the return. This may include for example, the return of the container by an authorized user other than the one by which it was taken. Alternatively the at least one processor may evaluate the time period that such container was outside the vault to determine if the time period is unduly long relative to the nature of the activity for which the container was removed. Alternatively or in addition, the at least one processor may operate to analyze the quantity of narcotic items that remain in the container at the time of return compared to the amount sensed at the time of removal. The change in quantity may be compared to other data accessible through the system, such as the nature and quantity of the prescription for the patient that was supposed to be filled as a result of the removal of narcotics from the container. If the quantity removed deviates from the quantity which is appropriate for the particular prescription this may also be noted. Further additional steps may be taken to notify the user or other persons of the deviation. Of course it should be understood that these approaches are exemplary.

As in the case with the monitoring of the system that is carried out when items are taken, when items are returned the system operates to monitor for the door of the vault to be closed and locked as represented by step 512. The closing of the door is sensed in a step 514. The events are logged as represented in step 515. The logging of such events results in all of the associated data being stored in the at least one data store 462. It should be understood that the operation of the system is schematically represented as exemplary and in other embodiments other approaches may be used.

Exemplary embodiments facilitate the tracking of the narcotics items stored in the vault. Further events related to the taking and return of the narcotics items are stored through operation of the computer 458. The output of the data through the display 464 facilitates the user's ability to locate medical items and to graphically verify that the taking and return of the medical item holding containers is noted by the system. This is done as the output from the display changes to indicate the presence or removal of item holding containers. Further the exemplary embodiment may operate to facilitate the locating of items in storage, such as by maintaining in the data store 462 the location of each of the narcotics items. Thus inputs by a user to the keyboard or mouse in connection with the system may enable a user to present a query and obtain an output which facilitates locating various medical items. Further in some embodiments the medical item holding containers can be returned to different storage locations from the ones that the containers were previously removed. This is because the exemplary system is flexible and enables the recording of the particular locations of each of the particular containers and the narcotics items stored therein.

Some further advantages of the exemplary embodiment include the ability to store information within the containers themselves. This may include the particular narcotics items stored therein as well as a detailed record of the activities associated with each container, including the users who removed it, the times of removal and return, the patients for whom items were taken and the quantities of items that were removed between the time of removal and return. Of course in other embodiments different or additional data may also be stored.

Further it should be understood that while in the exemplary embodiment communications between the containers and the readers and programming devices in the storage locations is accomplished through RF signals, in other embodiments other communications methodologies may be used. This may include for example, the use of infrared radiation or other suitable communications techniques. In addition it should be understood that in the exemplary embodiment the principles described in connection with monitoring the taking of items may also be utilized in connection with tracking other parameters. This may include for example the restocking or replenishment of items, the substitution or replacement of items or other activities associated with the use of the system. The programmable nature of the particular containers and system facilitates various types of tracking activities that enables various beneficial functions.

Thus the exemplary embodiments achieve at least some of the above stated objectives, eliminate difficulties encountered in the use of prior methods, solve problems and attains the desirable results described herein.

In the foregoing description certain terms have been used for brevity, clarity, and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following any feature described as a means for performing a function shall be construed as encompassing any means known to those skilled in the art to be capable of performing the recited function and shall not be limited to the structures shown herein or mere equivalents thereof.

Having described the features, discoveries and the principles of the invention, the manner in which it is constructed and operated and the advantages and useful results attained; the new and useful structures, device elements, arrangements, parts, combinations, systems, equipment, operations, methods and relationships are set forth in the appended claims.

I claim:

1. Apparatus comprising:
    at least one reader,
        wherein the at least one reader is operative to read identifying data that is usable to identify a user as an authorized user,
    a housing,
        wherein the housing bounds an interior area,
        wherein the housing includes an opening,
            wherein the opening provides access from outside the housing to the interior area,
    a door,
        wherein the door is movably mounted in operatively supported connection with the housing,
        wherein the door is movable between an open position and a closed position,
            wherein in the open position the interior area is accessible from outside the housing through the opening, and
            wherein in the closed position the door prevents access to the interior area from outside the housing through the opening,
    a lock,
        wherein the lock is in operative connection with the door,
        wherein the lock is changeable between a locked condition and an unlocked condition,
            wherein in the locked condition the lock is operative to hold the door in the closed position,
    a holder,
        wherein the holder includes a plurality of storage locations, wherein each storage location is configured to removably accept a narcotic item holding container therein,
wherein the holder is in operatively supported connection with the housing in the interior area,
a plurality of wireless readers,
wherein each wireless reader is positioned adjacent to a corresponding one of the storage locations,
a plurality of narcotic item holding containers,
wherein each container is operative to hold at least one unit of a narcotic item,
a plurality of wireless transmitters,
wherein each container is associated with a wireless transmitter,
wherein each respective wireless transmitter is operative to output at least one wireless signal,
wherein the at least one wireless signal is usable to identify at least one of a particular container and a narcotic item held by the particular container,
wherein each wireless reader adjacent a corresponding storage location is operative to receive at least one wireless signal from a wireless transmitter associated with a container when the container is positioned in the storage location, and
wherein the wireless reader is not operative to receive the at least one wireless signal from the wireless transmitter when the container is not positioned in the holder,
at least one processor,
wherein the at least one processor is in operative connection with the at least one reader, the lock, the plurality of wireless readers, and at least one data store which includes data corresponding to
identifying data for each of a plurality of authorized users, and
a plurality of narcotics items held by the containers,
wherein the at least one processor is operative to
cause the lock to change from the locked condition to the unlocked condition, responsive at least in part to the at least one reader reading authorization data corresponding to a first user, and
then cause to be stored in the at least one data store, data indicating that at least one of a first narcotic item and a first container containing the first narcotics item was removed from the housing by the first user, responsive at least in part to a wireless reader ceasing to receive at least one wireless signal from the wireless transmitter associated with the first container containing the first narcotics item,
a display in operative connection with the at least one processor,
wherein the at least one processor is operative to cause the display to output holder indicia that includes a visual representation of at least one narcotic item in each container in a respective storage location in the holder,
wherein the at least one processor is operative to cause the holder indicia to change to no longer indicate a representation of the first narcotic item in a storage location when the first container holding such first narcotic item is not in the storage location.

2. The apparatus according to claim 1 wherein each of the plurality of wireless readers is operative to receive at least one wireless signal from each of the plurality of wireless transmitters, wherein any of the plurality of containers are enabled to be placed in any of the plurality of storage locations in the holder.

3. The apparatus according to claim 1 wherein the holder is movably mounted in operatively supported connection with the housing, and is operative to extend through the opening when the door is in the open position, and further comprising:
at least one holder position sensor,
wherein the at least one holder position sensor is operative to sense when the holder is extended in the opening, and
wherein the at least one holder position sensor is in operative connection with the at least one processor, and
wherein the at least one processor is operative to cause the holder indicia to be output through the display responsive at least in part to the at least one holder position sensor sensing the holder is extended in the opening.

4. The apparatus according to claim 1 wherein each wireless reader comprises a radio frequency (RF) reader, and wherein each wireless transmitter comprises a RF transmitter.

5. The apparatus according to claim 1 wherein each container includes at least one weight sensor associated therewith, and wherein a respective wireless transmitter associated with a respective container is operative to produce at least one wireless signal corresponding to weight sensed by the at least one weight sensor associated with the respective container.

6. The apparatus according to claim 5 wherein the at least one processor is operative to cause to be stored in the at least one data store, data corresponding to the weight sensed by the at least one weight sensor associated with the respective container.

7. Apparatus comprising:
at least one reader,
wherein the at least one reader is operative to read identifying data that is usable to identify a user as an authorized user,
a housing,
wherein the housing bounds an interior area,
wherein the housing includes an opening,
wherein the opening provides access from outside the housing to the interior area,
a door,
wherein the door is movably mounted in operatively supported connection with the housing,
wherein the door is movable between an open position and a closed position,
wherein in the open position the interior area is accessible from outside the housing through the opening, and
wherein in the closed position the door prevents access to the interior area from outside the housing through the opening,
a lock,
wherein the lock is in operative connection with the door,
wherein the lock is changeable between a locked condition and an unlocked condition,
wherein in the locked condition the lock is operative to hold the door in the closed position,
a holder,
wherein the holder includes a plurality of storage locations,
wherein each storage location is configured to removably accept a narcotic item holding container therein,
wherein the holder is in operatively supported connection with the housing in the interior area,
a plurality of wireless readers, wherein each wireless reader is positioned adjacent to a corresponding one of the storage locations,
a plurality of narcotic item holding containers,
  wherein each container is operative to hold at least one unit of a narcotic item,
a plurality of wireless transmitters,
  wherein each container is associated with a wireless transmitter,
  wherein each respective wireless transmitter is operative to output at least one wireless signal,
    wherein the at least one wireless signal is usable to identify at least one of a particular container and a narcotic item held by the particular container,
wherein each wireless reader adjacent a corresponding storage location is operative to receive at least one wireless signal from a wireless transmitter associated with a container when the container is positioned in the storage location, and
  wherein the wireless reader is not operative to receive the at least one wireless signal from the wireless transmitter when the container is not positioned in the holder,
at least one processor,
  wherein the at least one processor is in operative connection with the at least one reader, the lock, the plurality of wireless readers, and at least one data store which includes data corresponding to
    identifying data for each of a plurality of authorized users, and
    a plurality of narcotics items held by the containers,
  wherein the at least one processor is operative to
    cause the lock to change from the locked condition to the unlocked condition, responsive at least in part to the at least one reader reading authorization data corresponding to a first user, and
    then cause to be stored in the at least one data store, data indicating that at least one of a first narcotic item and a first container containing the first narcotics item was removed from the housing by the first user, responsive at least in part to a wireless reader ceasing to receive at least one wireless signal from the wireless transmitter associated with the first container containing the first narcotics item,
a display in operative connection with the at least one processor,
  wherein the at least one processor is operative to cause the display to output holder indicia that includes a visual representation of at least one narcotic item in each container in a respective storage location in the holder,
wherein the holder comprises a drawer,
  wherein the drawer is movably mounted in operative supported connection with the housing,
  wherein the drawer is movable to extend in the opening when the door is in the open position,
a drawer position sensor,
  wherein the drawer position sensor is operative to sense the drawer extended in the opening, and
  wherein the drawer position sensor is in operative connection with the at least one processor,
    wherein the at least one processor is operative to cause the holder indicia to be output through the display responsive at least in part to the drawer position sensor.

8. The apparatus according to claim 7 wherein each wireless reader comprises a radio frequency (RF) reader, and wherein each wireless transmitter comprises a RF transmitter.

9. The apparatus according to claim 7 wherein each container includes at least one weight sensor associated therewith, and wherein a respective wireless transmitter associated with a respective container is operative to produce at least one wireless signal corresponding to weight sensed by the at least one weight sensor associated with the respective container.

10. The apparatus according to claim 9 wherein the at least one processor is operative to cause to be stored in the at least one data store, data corresponding to the weight sensed by the at least one weight sensor associated with the respective container.

11. Apparatus comprising:
at least one reader,
  wherein the at least one reader is operative to read identifying data that is usable to identify a user as an authorized user,
a housing,
  wherein the housing bounds an interior area,
  wherein the housing includes an opening,
    wherein the opening provides access from outside the housing to the interior area,
a door,
  wherein the door is movably mounted in operatively supported connection with the housing,
  wherein the door is movable between an open position and a closed position,
    wherein in the open position the interior area is accessible from outside the housing through the opening, and
    wherein in the closed position the door prevents access to the interior area from outside the housing through the opening,
a lock,
  wherein the lock is in operative connection with the door,
  wherein the lock is changeable between a locked condition and an unlocked condition,
    wherein in the locked condition the lock is operative to hold the door in the closed position,
a holder,
  wherein the holder includes a plurality of storage locations,
    wherein each storage location is configured to removably accept a narcotic item holding container therein,
  wherein the holder is in operatively supported connection with the housing in the interior area,
a plurality of wireless readers,
  wherein each wireless reader is positioned adjacent to a corresponding one of the storage locations,
a plurality of narcotic item holding containers,
  wherein each container is operative to hold at least one unit of a narcotic item,
a plurality of wireless transmitters,
  wherein each container is associated with a wireless transmitter,
  wherein each respective wireless transmitter is operative to output at least one wireless signal,
    wherein the at least one wireless signal is usable to identify at least one of a particular container and a narcotic item held by the particular container,
wherein each wireless reader adjacent a corresponding storage location is operative to receive at least one wireless signal from a wireless transmitter associated with a container when the container is positioned in the storage location, and wherein the wireless reader is not operative to receive the at least one wireless signal from the wireless transmitter when the container is not positioned in the holder, at least one processor, wherein the at least one processor is in operative connection with the at least one reader, the lock, the plurality of wireless readers, and at least one data store which includes data corresponding to identifying data for each of a plurality of authorized users, and a plurality of narcotics items held by the containers, wherein the at least one processor is operative to cause the lock to change from the locked condition to the unlocked condition, responsive at least in part to the at least one reader reading authorization data corresponding to a first user, and then cause to be stored in the at least one data store, data indicating that at least one of a first narcotic item and a first container containing the first narcotics item was removed from the housing by the first user, responsive at least in part to a wireless reader ceasing to receive at least one wireless signal from the wireless transmitter associated with the first container containing the first narcotics item, wherein each container includes an wireless receiver and programmable memory, wherein each storage location includes an wireless programming device operative to program the programmable memory of a container in the storage location, wherein the at least one processor is in operative connection with the wireless programming device of each storage location, wherein the at least one processor is operative to cause to be included in the programmable memory of a respective container, data corresponding to an authorized user who removes the respective container from a storage location.

12. The apparatus according to claim 11 wherein each wireless receiver comprises a radio frequency (RF) receiver, and wherein each wireless programming device comprises a RF programming device.

13. The apparatus according to claim 12 wherein the at least one processor is in operative connection with the RF programming device in each storage location, and wherein the at least one processor is operative to cause to be included in the programmable memory on the container, data corresponding to the first narcotic item stored in the container.

14. The apparatus according to claim 12 wherein the at least one data store includes patient data, and wherein the at least one processor is in operative connection with the RF programming device in each storage location, and wherein the at least one processor is operative to cause to be included in the programmable memory on the container, data corresponding to a patient for whom items were taken from the container.

15. The apparatus according to claim 11 wherein each container includes at least one weight sensor associated therewith, and wherein a respective wireless transmitter associated with a respective container is operative to produce at least one wireless signal corresponding to weight sensed by the at least one weight sensor associated with the respective container.

16. The apparatus according to claim 15 wherein the at least one processor is operative to cause to be stored in the at least one data store, data corresponding to the weight sensed by the at least one weight sensor associated with the respective container.

17. Apparatus comprising:

at least one reader, wherein the at least one reader is operative to read identifying data that is usable to identify a user as an authorized user, a housing, wherein the housing bounds an interior area, wherein the housing includes an opening, wherein the opening provides access from outside the housing to the interior area, a door, wherein the door is movably mounted in operatively supported connection with the housing, wherein the door is movable between an open position and a closed position, wherein in the open position the interior area is accessible from outside the housing through the opening, and wherein in the closed position the door prevents access to the interior area from outside the housing through the opening, a lock, wherein the lock is in operative connection with the door, wherein the lock is changeable between a locked condition and an unlocked condition, wherein in the locked condition the lock is operative to hold the door in the closed position, a holder, wherein the holder includes a plurality of storage locations, wherein each storage location is configured to removably accept a narcotic item holding container therein, wherein the holder is in operatively supported connection with the housing in the interior area, a plurality of wireless readers, wherein each wireless reader is positioned adjacent to a corresponding one of the storage locations, a plurality of narcotic item holding containers, wherein each container is operative to hold at least one unit of a narcotic item, a plurality of wireless transmitters, wherein each container is associated with a wireless transmitter, wherein each respective wireless transmitter is operative to output at least one wireless signal, wherein the at least one wireless signal is usable to identify at least one of a particular container and a narcotic item held by the particular container, wherein each wireless reader adjacent a corresponding storage location is operative to receive at least one wireless signal from a wireless transmitter associated with a container when the container is positioned in the storage location, and wherein the wireless reader is not operative to receive the at least one wireless signal from the wireless transmitter when the container is not positioned in the holder, at least one processor, wherein the at least one processor is in operative connection with the at least one reader, the lock, the plurality of wireless readers, and at least one data store which includes data corresponding to identifying data for each of a plurality of authorized users, and a plurality of narcotics items held by the containers, wherein the at least one processor is operative to
   cause the lock to change from the locked condition to
      the unlocked condition, responsive at least in part
      to the at least one reader reading authorization data
      corresponding to a first user, and
   then cause to be stored in the at least one data store,
      data indicating that at least one of a first narcotic
      item and a first container containing the first narcotics item was removed from the housing by the
      first user, responsive at least in part to a wireless
      reader ceasing to receive at least one wireless signal
      from the wireless transmitter associated with the
      first container containing the first narcotics item,
wherein each container includes an wireless receiver and programmable memory,
wherein each storage location includes an wireless programming output device operative to program the programmable memory of a container in the storage location,
wherein the at least one processor includes at least one timing function operating therein,
   wherein the at least one processor is in operative connection with the wireless programming output device in each storage location,
   wherein the at least one processor is operative to cause to be included in the programmable memory of a respective container, data corresponding to a time the respective container was removed from a storage location.

18. The apparatus according to claim 17 wherein each wireless receiver comprises a radio frequency (RF) receiver, and wherein each wireless programming device comprises a RF programming device.

19. The apparatus according to claim 17 wherein each container includes at least one weight sensor associated therewith, and wherein a respective wireless transmitter associated with a respective container is operative to produce at least one wireless signal corresponding to weight sensed by the at least one weight sensor associated with the respective container.

20. The apparatus according to claim 19 wherein the at least one processor is operative to cause to be stored in the at least one data store, data corresponding to the weight sensed by the at least one weight sensor associated with the respective container.

21. Apparatus comprising:
at least one reader,
   wherein the at least one reader is operative to read identifying data that is usable to identify a user as an authorized user,
a housing,
   wherein the housing bounds an interior area,
   wherein the housing includes an opening,
      wherein the opening provides access from outside the housing to the interior area,
a door,
   wherein the door is movably mounted in operatively supported connection with the housing,
   wherein the door is movable between an open position and a closed position,
      wherein in the open position the interior area is accessible from outside the housing through the opening, and
      wherein in the closed position the door prevents access to the interior area from outside the housing through the opening,
a lock,
   wherein the lock is in operative connection with the door,
   wherein the lock is changeable between a locked condition and an unlocked condition,
      wherein in the locked condition the lock is operative to hold the door in the closed position,
a holder,
   wherein the holder includes a plurality of storage locations,
      wherein each storage location is configured to removably accept a narcotic item holding container therein,
   wherein the holder is in operatively supported connection with the housing in the interior area,
a plurality of wireless readers,
   wherein each wireless reader is positioned adjacent to a corresponding one of the storage locations,
a plurality of narcotic item holding containers,
   wherein each container is operative to hold at least one unit of a narcotic item,
a plurality of wireless transmitters,
   wherein each container is associated with a wireless transmitter,
   wherein each respective wireless transmitter is operative to output at least one wireless signal,
      wherein the at least one wireless signal is usable to identify at least one of a particular container and a narcotic item held by the particular container,
wherein each wireless reader adjacent a corresponding storage location is operative to receive at least one wireless signal from a wireless transmitter associated with a container when the container is positioned in the storage location, and
wherein the wireless reader is not operative to receive the at least one wireless signal from the wireless transmitter when the container is not positioned in the holder,
at least one processor,
   wherein the at least one processor is in operative connection with the at least one reader, the lock, the plurality of wireless readers, and at least one data store which includes data corresponding to
      identifying data for each of a plurality of authorized users, and
      a plurality of narcotics items held by the containers,
   wherein the at least one processor is operative to
      cause the lock to change from the locked condition to
         the unlocked condition, responsive at least in part
         to the at least one reader reading authorization data
         corresponding to a first user, and
      then cause to be stored in the at least one data store,
         data indicating that at least one of a first narcotic
         item and a first container containing the first narcotics item was removed from the housing by the
         first user, responsive at least in part to a wireless
         reader ceasing to receive at least one wireless signal
         from the wireless transmitter associated with the
         first container containing the first narcotics item,
wherein each container includes an wireless receiver and programmable memory,
wherein each storage location includes an wireless programming output device operative to program the programmable memory of a container in the storage location,
wherein the at least one processor includes at least one timing function operating therein, wherein the at least one processor is in operative connection with the wireless programming output device in each storage location, wherein the at least one processor is operative to cause to be included in the programmable memory of a respective container, data corresponding to a time the respective container was placed in a storage location.

22. The apparatus according to claim 21 wherein each wireless receiver comprises a radio frequency (RF) receiver, and wherein each wireless programming device comprises a RF programming device.

23. The apparatus according to claim 21 wherein each container includes at least one weight sensor associated therewith, and wherein a respective wireless transmitter associated with a respective container is operative to produce at least one wireless signal corresponding to weight sensed by the at least one weight sensor associated with the respective container.

24. The apparatus according to claim 23 wherein the at least one processor is operative to cause to be stored in the at least one data store, data corresponding to the weight sensed by the at least one weight sensor associated with the respective container.

* * * * *